(12) United States Patent
Draghici et al.

(10) Patent No.: US 11,515,000 B2
(45) Date of Patent: Nov. 29, 2022

(54) GENETIC, METABOLIC AND BIOCHEMICAL PATHWAY ANALYSIS SYSTEM AND METHODS

(71) Applicant: Wayne State University, Detroit, MI (US)

(72) Inventors: Sorin Draghici, Detroit, MI (US); Zhonghui Xu, Detroit, MI (US); Michele Donato, Detroit, MI (US)

(73) Assignee: Wayne State University, Detroit, MI (US)

( * ) Notice: Subject to any disclaimer, the term of this patent is extended or adjusted under 35 U.S.C. 154(b) by 663 days.

(21) Appl. No.: 16/375,304

(22) Filed: Apr. 4, 2019

(65) Prior Publication Data

US 2019/0304567 A1  Oct. 3, 2019

Related U.S. Application Data

(63) Continuation of application No. 14/103,158, filed on Dec. 11, 2013, now Pat. No. 10,395,756.
(Continued)

(51) Int. Cl.
*G06G 7/48* (2006.01)
*G16B 5/20* (2019.01)
(Continued)

(52) U.S. Cl.
CPC .......... *G16B 5/20* (2019.02); *G16B 5/00* (2019.02); *G16B 20/20* (2019.02); *G06F 30/00* (2020.01); *G16B 20/00* (2019.02)

(58) Field of Classification Search
CPC ......... G06F 30/00; G16B 20/00; G16B 20/20; G16B 5/00; G16B 5/20
See application file for complete search history.

(56) References Cited

U.S. PATENT DOCUMENTS

2007/0009923 A1* 1/2007 Nolan ............... G01N 33/5091
                                                   435/6.13
2007/0038385 A1* 2/2007 Nikolskaya ............ G16B 50/20
                                                   702/19
(Continued)

OTHER PUBLICATIONS

Papin, Jason A., and Bernhard O. Palsson. "Topological analysis of mass-balanced signaling networks: a framework to obtain network properties including crosstalk." Journal of theoretical biology 227.2 (2004): 283-297.*

*Primary Examiner* — Rehana Perveen
*Assistant Examiner* — Nithya J. Moll
(74) *Attorney, Agent, or Firm* — Harness, Dickey & Pierce, P.L.C.

(57) ABSTRACT

Identifying pathways that are significantly impacted in a given condition is a crucial step in the understanding of the underlying biological phenomena. All approaches currently available for this purpose calculate a p-value that aims to quantify the significance of the involvement of each pathway in the given phenotype. These p-values were previously thought to be independent. Here, we show that this is not the case, and that pathways can affect each other's p-values through a "crosstalk" phenomenon that affects all major categories of existing methods. We describe a novel technique able to detect, quantify, and correct crosstalk effects, as well as identify novel independent functional modules. We assessed this technique on data from four real experiments coming from three phenotypes involving two species.

18 Claims, 20 Drawing Sheets

Related U.S. Application Data

(60) Provisional application No. 61/735,732, filed on Dec. 11, 2012.

(51) Int. Cl.
    *G16B 5/00*           (2019.01)
    *G16B 20/20*        (2019.01)
    *G16B 20/00*        (2019.01)
    *G06F 30/00*        (2020.01)

(56) References Cited

U.S. PATENT DOCUMENTS

| | | | |
|---|---|---|---|
| 2009/0182513 A1* | 7/2009 | Draghici | G16B 25/10 702/19 |
| 2011/0191087 A1* | 8/2011 | Lehrach | G06F 17/10 703/11 |
| 2012/0041683 A1* | 2/2012 | Vaske | G16B 5/20 702/19 |

\* cited by examiner

| rank | pathway | pval (fdr) |
|---|---|---|
| 1 | Parkinson's disease | 2.0e-05 |
| 2 | Alzheimer's disease | 3.6e-06 |
| 3 | Huntington's disease | 3.4e-05 |
| 4 | Leishmaniasis | 0.0003 |
| 5 | Phagosome | 0.0006 |
| 6 | Cell cycle | 0.0011 |
| 7 | Oocyte meiosis | 0.0016 |
| 8 | Cardiac muscle contraction | 0.0016 |
| 9 | Toll-like receptor | 0.0018 |
| 10 | PPAR signaling pathway | 0.0018 |
| 11 | Chemokine signaling pathway | 0.0018 |
| 12 | Lysosome | 0.0211 |
| 13 | B cell receptor | 0.0252 |
| 14 | Systemic lupus erythematosus | 0.0292 |
| 15 | Compl. and coag. cascades | 0.0342 |
| 16 | Cytokine-cytokine rec. inter. | 0.0342 |
| 17 | Chagas disease | 0.0466 |
| 18 | Progest. med. oocyte matur. | 0.0530 |
| 19 | Fc epsilon RI signaling pathway | 0.0548 |
| 20 | Leukocyte transendoth migr. | 0.0548 |

Fig. 1a

| rank | pathway | p(fdr) |
|---|---|---|
| 1 | Mitochondrial Activity | 8.13-10 |
| 2 | Phagosome | 9.3e-09 |
| 3 | Cellcycl+Oocyteme | 5.8e-08 |
| 4 | PPAR signaling pathway | 0.001 |
| 5 | Compl. C.C.+Systemic L.E. | 0.002 |
| 6 | *Cytok.-cytok. rec. int. | 0.043 |
| 7 | Toll-like receptor signaling | 0.051 |
| 8 | MAPK signaling pathway | 0.115 |
| 9 | B-cell receptor signaling | 0.145 |
| 10 | Lysome | 0.187 |
| 11 | Nat. killer cell med. cytotox | 0.187 |
| 12 | *Cell cycle | 0.229 |
| 13 | Calcium signaling pathway | 0.229 |
| 14 | Cell adhesion molecules | 0.258 |
| 15 | NOD-like receptor signaling | 0.258 |
| 16 | Vasc. smooth muscle contr. | 0.424 |
| 17 | Dilated cardiomyopathy | 0.424 |
| 18 | *Oocyte meiosis | 0.432 |
| 19 | Type I diabetes mellitus | 0.432 |
| 20 | Wnt signaling pathway | 0.476 |

Fig. 1b

|  | DE | NDE | Total |
|---|---|---|---|
| $P_j$ | $n_j$ | $m_j$ | $n_j + m_j$ |
| $P_j^c$ | $n - n_j$ | $m - m_j$ | $(n+m) - (n_j + m_j)$ |
| Total | $n$ | $m$ | $n + m$ |

Fig. 7a

|  | DE | NDE | Total |
|---|---|---|---|
| $P_{i/j}$ | $n_{i/j}$ | $m_{i/j}$ | $n_{i/j} + m_{i/j}$ |
| $(P_{i/j})^c$ | $n - n_{i/j}$ | $m - m_{i/j}$ | $(n+m) - (n_{i/j} + m_{i/j})$ |
| Total | $n$ | $m$ | $n + m$ |

Fig. 7b

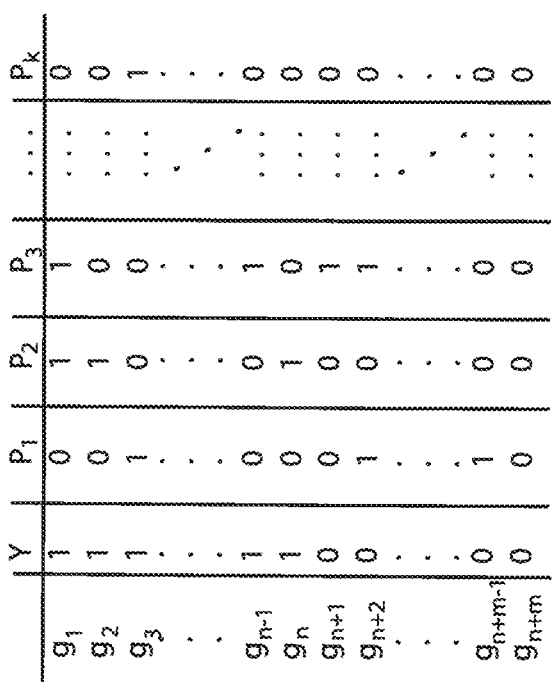

| rank | pathway | p(FDR) |
|---|---|---|
| 1 | Parkinson's disease | 7.2e-06 |
| 2 | Huntington's disease | 4.2e-05 |
| 3 | Alzheimer's disease | 0.0002 |
| 4 | Cell cycle | 0.0044 |
| 5 | Cardiac muscle contraction | 0.0087 |
| 6 | p53 signaling pathway | 0.0134 |
| 7 | PPAR signaling pathway | 0.0773 |
| 8 | Gap junction | 0.0920 |
| 9 | Progest. mediated oocyte matur. | 0.0995 |
| 10 | Oocyte meiosis | 0.1327 |
| 11 | Salivary secretion | 0.1442 |
| 12 | Cell adhesion molecules (CAMs) | 0.2390 |
| 13 | SNARE inter. in vesicular transp. | 0.2969 |
| 14 | Prostate cancer | 0.3837 |
| 15 | Vasopressin-reg. water reabs. | 0.5111 |
| 16 | Arrhythm. right ventr. card. | 0.5111 |
| 17 | Hedgehog signaling pathway | 0.5174 |
| 18 | Prion diseases | 0.5420 |
| 19 | Melanogenesis | 0.5432 |
| 20 | Pathways in cancer | 0.5432 |

Fig. 14a

| rank | pathway | p(FDR) |
|---|---|---|
| 1 | Mitochondrial Activity | 2.3e-08 |
| 2 | Arr. right ventr. cardiom. (ARVC) | 0.001 |
| 3 | Cell cycle | 0.001 |
| 4 | PPAR signaling pathway | 0.015 |
| 5 | Cell adhesion molecules (CAMs) | 0.019 |
| 6 | Melanogenesis | 0.019 |
| 7 | Vascular smooth muscle contr. | 0.080 |
| 8 | p53 signaling pathway | 0.125 |
| 9 | Pathways in cancer | 0.562 |
| 10 | SNARE inter. in vesicular transp. | 0.562 |
| 11 | Chagas disease | 0.575 |
| 12 | Long-term potentiation | 0.575 |
| 13 | Phagosome | 0.588 |
| 14 | Vasopressin-reg. water reabs. | 0.765 |
| 15 | Hedgehog signaling pathway | 0.765 |
| 16 | Dorso-ventral axis formation | 0.765 |
| 17 | Intest. imm. netw. for IgA prod. | 0.784 |
| 18 | Wnt signaling pathway | 0.984 |
| 19 | ECM-receptor interaction | 0.984 |
| 20 | Phototransduction | 0.984 |

Fig. 14b

| rank | pathway | p(FDR) |
|---|---|---|
| 1 | ECM-rec. interaction | 0.0343 |
| 2 | Focal adhesion | 0.0401 |
| 3 | Pathways in cancer | 0.0401 |
| 4 | Small cell lung cancer | 0.0401 |
| 5 | Axon guidance | 0.0401 |
| 6 | Prostate cancer | 0.0401 |
| 7 | Jak-STAT signaling pathway | 0.0401 |
| 8 | Progest.-med. oocyte mat. | 0.0951 |
| 9 | Adipocytokine signaling | 0.0951 |
| 10 | Melanoma | 0.1208 |
| 11 | Graft-versus-host disease | 0.1291 |
| 12 | Reg. of actin cytoskeleton | 0.2020 |
| 13 | Aldosterone-reg. Na reabs. | 0.2020 |
| 14 | Oocyte meiosis | 0.2168 |
| 15 | Long-term depression | 0.2174 |
| 16 | mTOR signaling pathway | 0.3048 |
| 17 | Nat. killer cell med. cytotox. | 0.3185 |
| 18 | Vibrio cholerae infection | 0.3225 |
| 19 | SNARE inter. in vesicular trans. | 0.3699 |
| 20 | Salivary secretion | 0.3699 |

Fig. 15a

| rank | pathway | p(FDR) |
|---|---|---|
| 1 | Jak-STAT signaling pathway | 5e-09 |
| 2 | Integrin Mediated ECM Sign. | 0.0001 |
| 3 | Axon guidance | 0.0036 |
| 4 | Vascular sm. muscle contr. | 0.0070 |
| 5 | Aldosterone-reg. N a reabs. | 0.0190 |
| 6 | Adipocytokine signaling | 0.0326 |
| 7 | Nat. killer cell med. cytotox. | 0.0344 |
| 8 | Regulation of actin cytosk. | 0.1403 |
| 9 | Compl. and coag. cascades | 0.3413 |
| 10 | Adherens junction | 0.3413 |
| 11 | SNARE interac. in ves. trans. | 0.4842 |
| 12 | Circadian rhythm - mammal | 0.5074 |
| 13 | Lysosome | 0.6552 |
| 14 | Protein proc. in endoplasmic ret. | 0.7182 |
| 15 | Vibrio cholerae infection | 0.7182 |
| 16 | * * * Focal adhesion | 0.9844 |
| 17 | Type I diabetes mellitus | 1 |
| 18 | Phagosome | 1 |
| 19 | Huntington's disease | 1 |
| 20 | Cell cycle | 1 |

Fig. 15b

| | $g_1$ | $g_2$ | $g_3$ | ... | $g_{n-1}$ | $g_n$ | $g_{n+1}$ | $g_{n+2}$ | ... | $g_{n+m-1}$ | $g_{n+m}$ |
|---|---|---|---|---|---|---|---|---|---|---|---|
| Y | 1 | 1 | 1 | ... | 1 | 1 | 0 | 0 | ... | 0 | 0 |
| $P_1$ | 0 | 0 | 1 | ... | 0 | 0 | 0 | 1 | ... | 1 | 0 |
| $P_2$ | 1 | 1 | 0 | ... | 0 | 1 | 0 | 0 | ... | 0 | 0 |
| $P_3$ | 1 | 0 | 0 | ... | 1 | 0 | 1 | 1 | ... | 0 | 0 |
| ⋮ | ⋮ | ⋮ | ⋮ | ... | ⋮ | ⋮ | ⋮ | ⋮ | ... | ⋮ | ⋮ |
| $P_k$ | 0 | 0 | 1 | ... | 0 | 0 | 0 | 0 | ... | 0 | 0 |

Fig. 18

GENETIC, METABOLIC AND BIOCHEMICAL PATHWAY ANALYSIS SYSTEM AND METHODS

CROSS-REFERENCE TO RELATED APPLICATIONS

This application is a continuation of U.S. patent application Ser. No. 14/103,158, filed on Dec. 11, 2013, which claims the benefit of U.S. Provisional Application No. 61/735,732, filed on Dec. 11, 2012. The entire disclosures of the above applications are incorporated herein by reference.

GOVERNMENT RIGHTS

This invention was made with government support under R01 DK089167 awarded by National Institutes of Health. The government has certain rights in the invention.

FIELD

The present disclosure relates generally to biomolecular networks made up of biomolecular nodes, such as genes, transcripts, gene products, RNA, mRNA, miRNA, proteins and biochemical compounds. Additionally the present disclosure relates to subsystems of such biomolectular nodes with defined properties, such as metabolic and signaling pathways. More particularly the disclosure relates to computer-implemented bioinformatics techniques for analysis and for correction of crosstalk effects in node subsystem and pathway analysis.

BACKGROUND

U.S. Pat. No. 8,068,994 describes a method of performing impact analysis of genes (or proteins or metabolites or reactants) that are different between different phenotypes Without limitation, such phenotypes can be disease tissue vs. healthy tissue, treated with a drug vs. untreated, treated with drug A vs. treated with drug B, different time points in a time series measuring changes after a given intervention, etc. Without loss of generality, we will henceforth refer to the illustrative example of a phenotype comparison between disease and healthy.

The biological pathway(s) impacted in a disease state are predicted by (a) providing expression level data for a plurality of biomolecules differentially expressed in the disease state, compared with same biomolecules expressed in the healthy state; (b) determining the significance of the changes in the levels of the biomolecules in disease state; (c) determining the effect(s) of each biomolecule from the plurality of biomolecules on the expression of different downstream biomolecules within each pathway to provide a perturbation factor for each biomolecule in the pathway; (d) combining statistical significance of differentially expressed biomolecules present in the disease state, with a sum of perturbation factors for all of the biomolecules, generating an impact factor for each pathway; (e) calculating statistical significance of the observed impact factor based upon determined probability of having statistical significant presence of differentially expressed biomolecules in step (b) and the sum of perturbation factors in step (c); and (f) outputting statistical significance of the involvement of the pathway(s) in the given phenotype.

While the techniques disclosed in U.S. Pat. No. 8,068, 994, work well, We have discovered that when conducting pathway analysis it is important to identify the interactions between different pathways that are significantly impacted in a given condition. None of the existing techniques are able to accomplish this. Currently available approaches calculate a p-value that aims to quantify the significance of the involvement of each pathway in the given phenotype. These p-values have traditionally been thought to be independent. We have discovered however, as the remainder of this disclosure will explain, that pathways can affect each other's p-values through a phenomena we call "crosstalk." This disclosure also describes the first method able to: i) detect the presence of such crosstalk, ii) quantify its extent and iii) assess the impact on a pathway after removing this crosstalk effect.

SUMMARY

This section provides a general summary of the disclosure, and is not a comprehensive disclosure of its full scope or all of its features.

In one aspect, the disclosed computer-implemented system and method i) detect cross-talk phenomena, ii) quantify the amounts of such crosstalk and iii) correct for it. The disclosed method and system for crosstalk analysis involve several steps that may be performed separately or combined.

First, a crosstalk matrix is computed, taking into account an analysis of pairwise crosstalk interactions between pathways in a given condition. The matrix is useful, for example, in producing a heat map visualization showing the p-value of each pathway when the effect of genes from each other pathway are removed. Through this visualization the extent of crosstalk effects can be better analyzed.

Second, sub-pathways are identified through a module detection step that identifies sub-pathways that appear to be involved in the specific condition studied. This allows a sub-pathway to be studied independently of the pathway to which they belong.

Third, maximum impact estimation is performed, where the biological impact of each gene is assigned to only one of the pathways to which the gene belongs.

The second and third steps collectively create a new set of pathways that are not affected by crosstalk effects.

In a fourth step, new p-values can be computed for each pathway, building a ranked list from which false positives due to crosstalk have been removed.

Computation of the crosstalk matrix may be performed using a computer to construct an impact matrix whereby each gene contributes to one and only one pathway. The computer is then used to process the impact matrix by applying a likelihood-based estimation upon the impact matrix and thereby identify a new set of pathways that is not affected by crosstalk effects.

In another aspect, disclosed is a computer-implemented apparatus for studying biomolecular networks made up of biomolecular nodes that are linked as a plurality of nodes that define a pathway associated with a designated physical condition mediated by that pathway. The apparatus comprises a memory circuit configured to define the following data structures:

(a) a node data structure storing data representing a node as having an associated measured difference attribute capable of being selectively set to one of a first state and a second state;

(b) a pathway data structure storing data representing plural pathways each pathway comprising a plurality of linked nodes as represented by said node data structure;

(c) a p-value data structure storing data in association with the pathway data structure representing probability values (p-values) indicating the probability that a pathway relates to a designated physical condition mediated by that pathway.

The apparatus further comprises at least one processor coupled to read and write data in and out of said memory circuit, where the at least one processor is programmed to execute the following operations:

(a) populate the pathway data structure and node data structure with data corresponding to at least a first pathway and a second pathway;

b) manipulate the data stored in the pathway and node data structures to compute a p-value and store the computed p-values as first p-value data in the p-value data structure;

(c) manipulate the data stored in the pathway and node data structures to identify and remove from the pathway data structure intersecting nodes that are common to both first and second pathways to thereby define a modified data set;

(d) manipulate the modified data set to compute a p-value and store the computed p-values as second p-value data in the p-value data structure;

(e) compare the stored first and second p-value data and based on the comparison makes a determination whether crosstalk is present between the first and second pathways according to whether the first and second p-values differ from one another; and (f) provide an indication to a user of the apparatus of whether crosstalk is present between the first and second pathways.

In yet another aspect the processor(s) of the computer-implemented apparatus is programmed to analyze the presence of crosstalk between the first and second pathways based on said comparison of the respective p-values according to the following calculus:

(a) if the first and second p-values are substantially unchanged when the intersecting nodes are removed, provide an indication to a user that no crosstalk is present;

(b) one and only one of the first and second p-values decreases when the intersecting nodes are removed, provide an indication to a user that crosstalk is present;

(c) one and only one of the first and second p-values increases when the intersecting nodes are removed, provide an indication to a user that crosstalk is present;

(d) if the first and second p-values both decrease when the intersecting nodes are removed, provide an indication to a user that an independent functional module is involved in the designated physical condition.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1a and 1b illustrate the results of ORA analysis in a fat remodeling experiment for the comparison between day 3 and day 0. FIG. 1a shows the results before correction for crosstalk effects; FIG. 1b shows the results after correction for crosstalk effects. All p-values have been FDR-corrected.

Figures 4A, 4B:
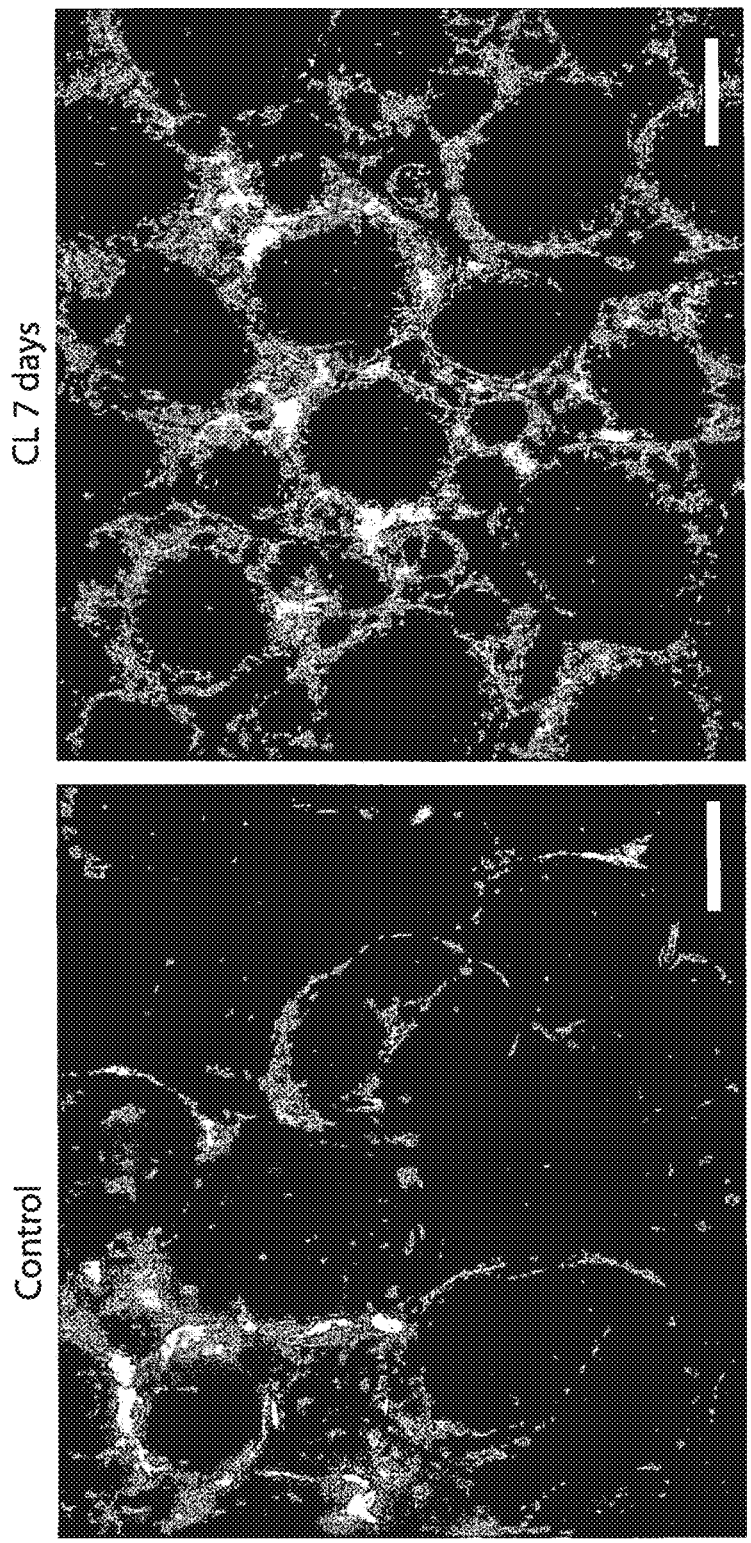

FIGS. 4a and 4b are photomicrograph images of ependymal white adipose tissue of a control mouse; FIG. 4a of a control mouse and FIG. 4b of a mouse treated with CL for 7 days, showing that the treatment triggered massive mitochondrial biogenesis, demonstrating in vivo that indeed, the mitochondrial pathway is central in this experiment. The white bar scale in both figures represents a 20 micron length.

Figure 5A:
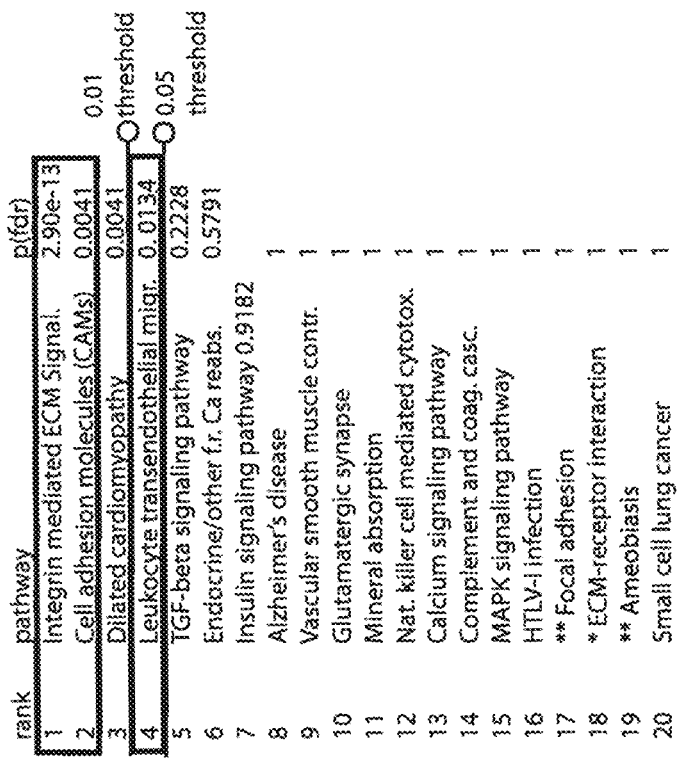
Figure 5B:
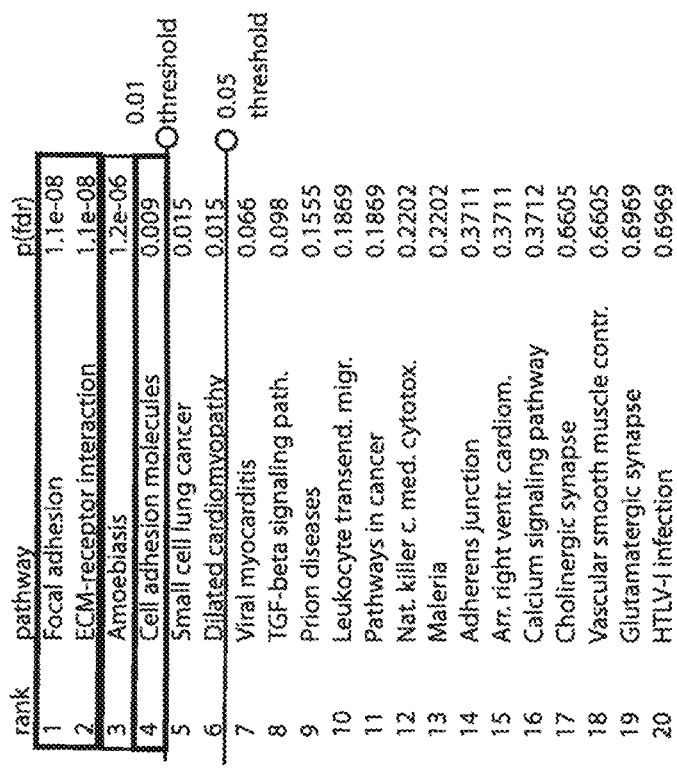

FIGS. 5a and 5b illustrate the ORA results for the cervical ripening experiment, FIG. 5a showing before and FIG. 5b showing after the correction for crosstalk effects. All p-values are FDR-corrected.

Figure 6:
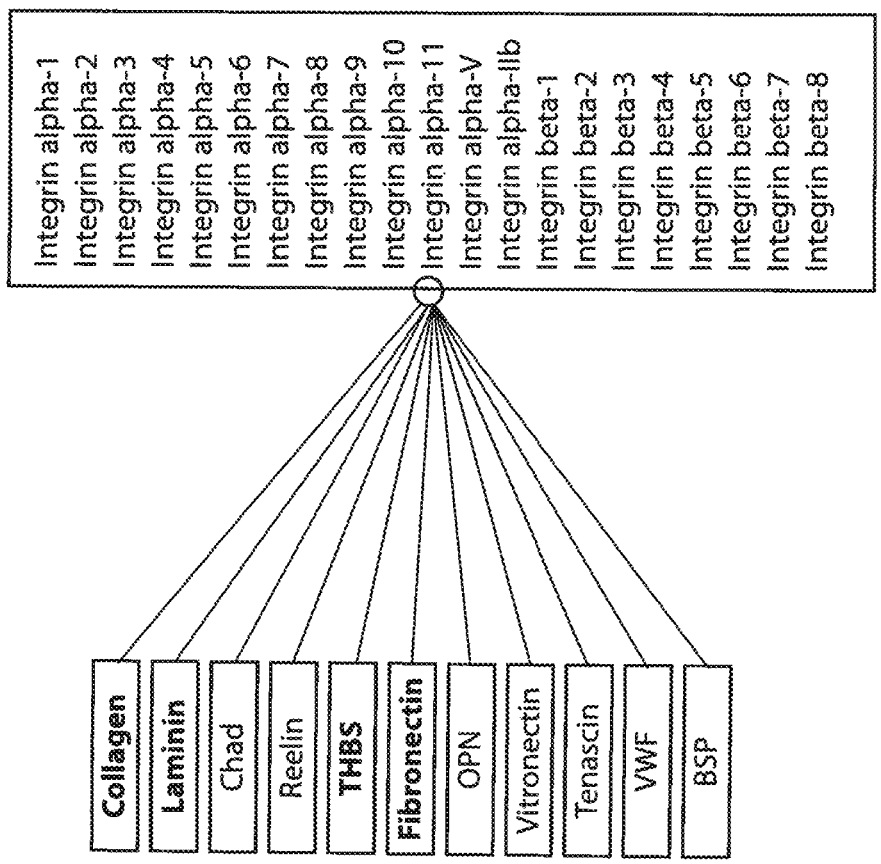

FIG. 6 depicts the novel Integrin-Mediated ECM Signaling. This new module was found to be independently activated and statistically significant in two different conditions: hormone treatment of post-menopausal women and cervical ripening in normal pregnancies. Genes shown in Bold were found to be differentially expressed in the hormone treatment experiment.

FIGS. 7a and 7b are tables comparing the classical over-representation analysis (FIG. 7a) with the crosstalk matrix analysis proposed here (FIG. 7b).

Figure 8:
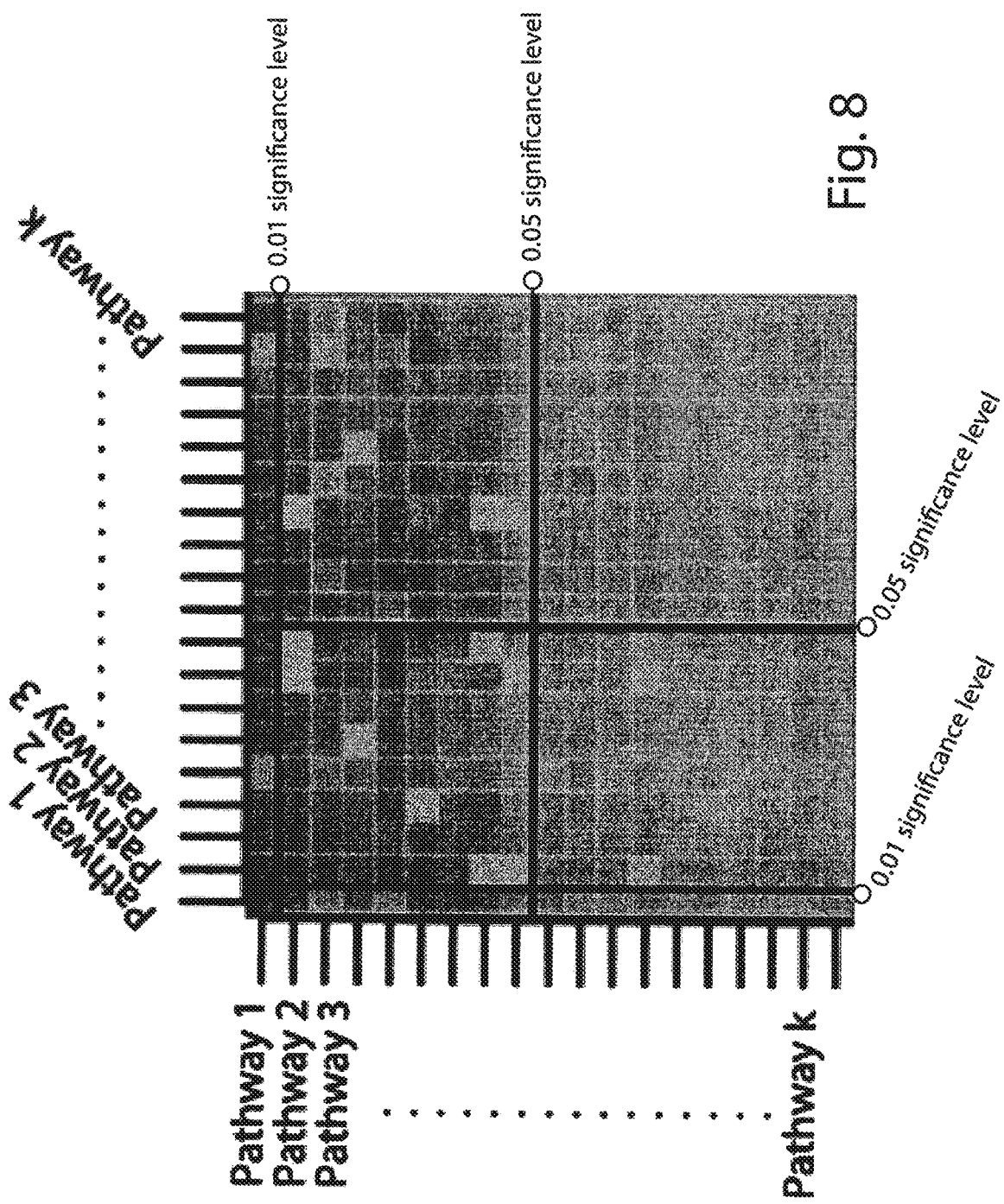

FIG. 8 is an exemplary crosstalk matrix. The p-values in the matrix have been log-transformed (base 10 log) and the sign of the result has been inverted.

FIG. 9 is an example of a DE/membership matrix. The column Y represents the indicator of differential expression of the various genes (1 for the nDE genes and 0 for the m NDE genes). Column $P_j$ represents the membership indicator for pathway j. Row $g_i$ describes genes i in terms of its differential expression and its membership to the various pathways.

Figures 10A, 10B, 10C:
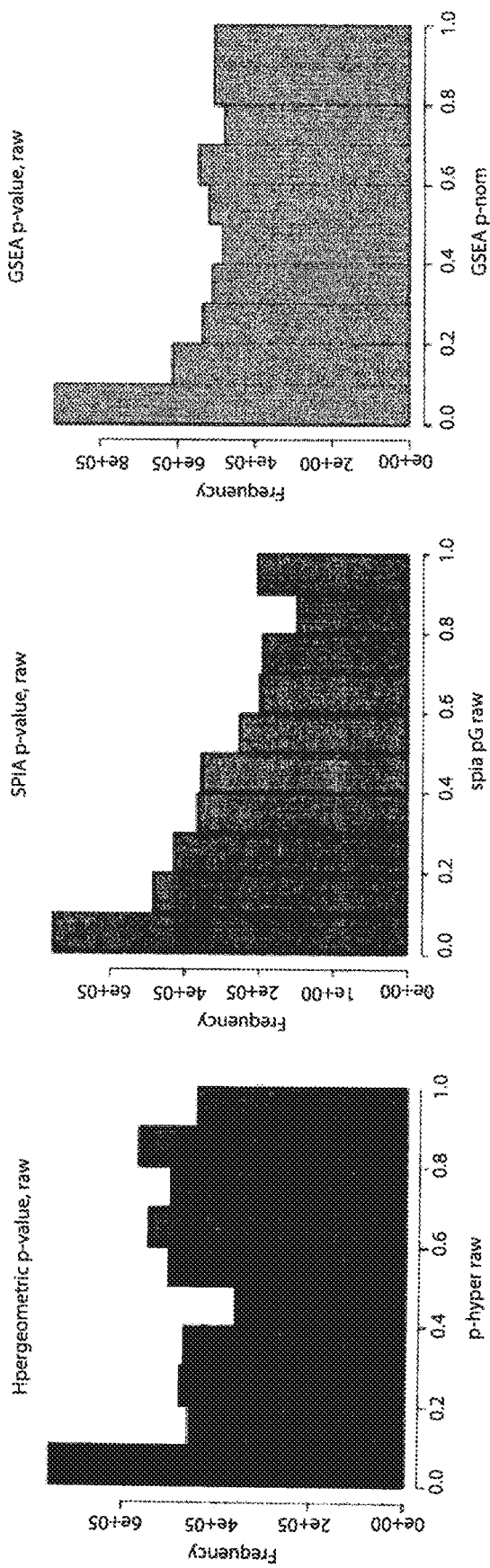

FIGS. 10a, 10b and 10c (collectively FIG. 10) are graphs depicting the distributions of p-values obtained from three different analysis methods under the null hyptothesis: hypergeometric (left), SPIA (middle) and GSEA (right). All three exhibit a significant departure from the expected uniform distribution (Kolmogorov-Smirnov p-values of the order of $10^{-16}$ in all cases). Notably all methods yield a much higher than expected number of pathways with p-values lower than 0.1, i.e. false positives.

Figure 11:
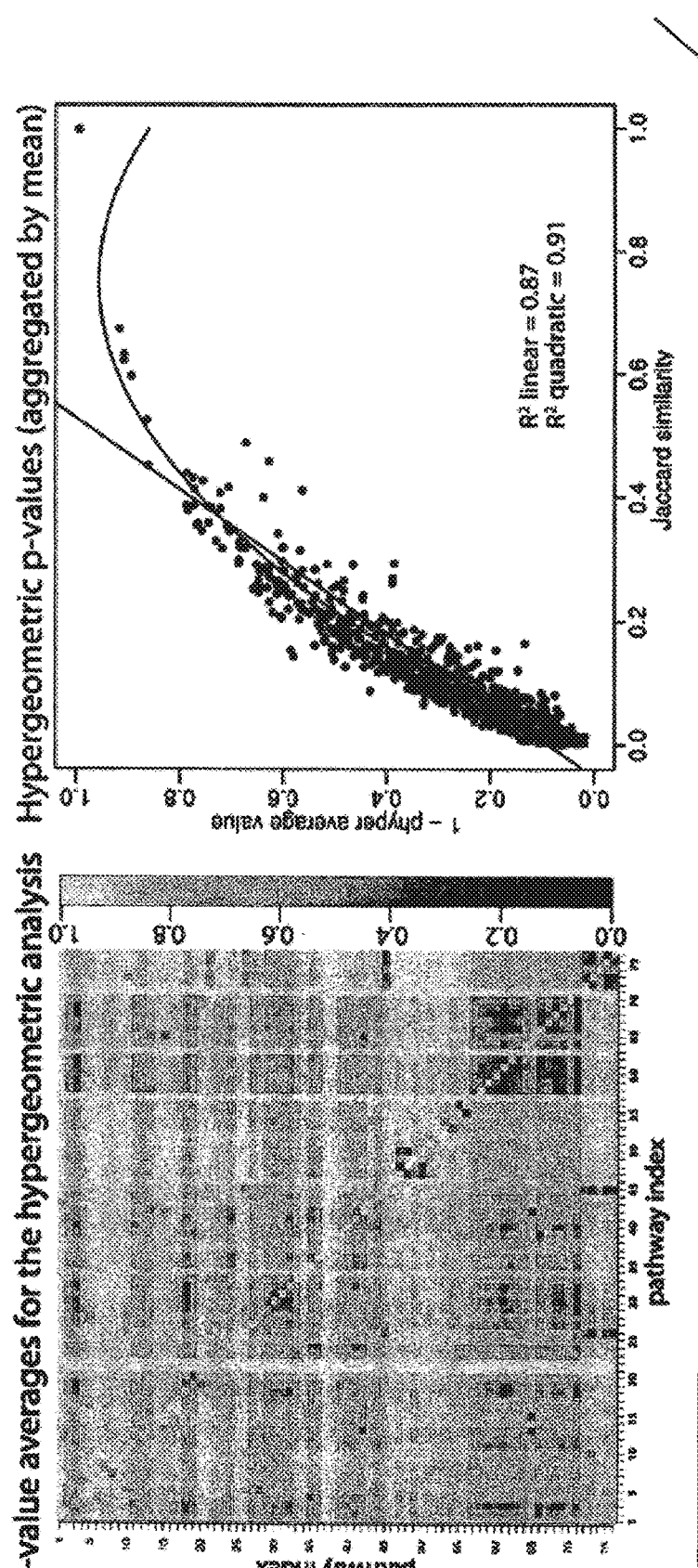

FIG. 11 are graphs showing pathway coupling in the hpergeometric analysis. The left panel shows a number of random genes were chosen from a "bait" pathway i such that its hypergeometric p-value is 0.01. Other genes were chosen randomly from all other pathways (acting as preys), up to a constant number (n=100). The elements [i, j] where i=6 j represent the mean of the distribution of p-values for 1000 random trials using pathway i as bait and pathway j as prey. The elements [i, i] (on the diagonal) represent the classical hypergeometric p-value of pathway i. The data show that a considerable number of pathways influence each other through a "coupling" of the p-values. For instance, row 3 of the matrix shows that when pathway 3 is chosen to be significant, several other pathways (e.g. columns 57 to 70) also tend to be significant (dark shades of blue represent significant p-values). Right panel: each point represents the average of the p-values of all the random trials for pairs with the same Jaccard index. The lines represent the fitting of linear and a quadratic models. Both models show a strong dependence between the p-value coupling and the Jaccard index. Similar results were obtained for GSEA and impact analysis (see FIG. 12).

Figure 12:
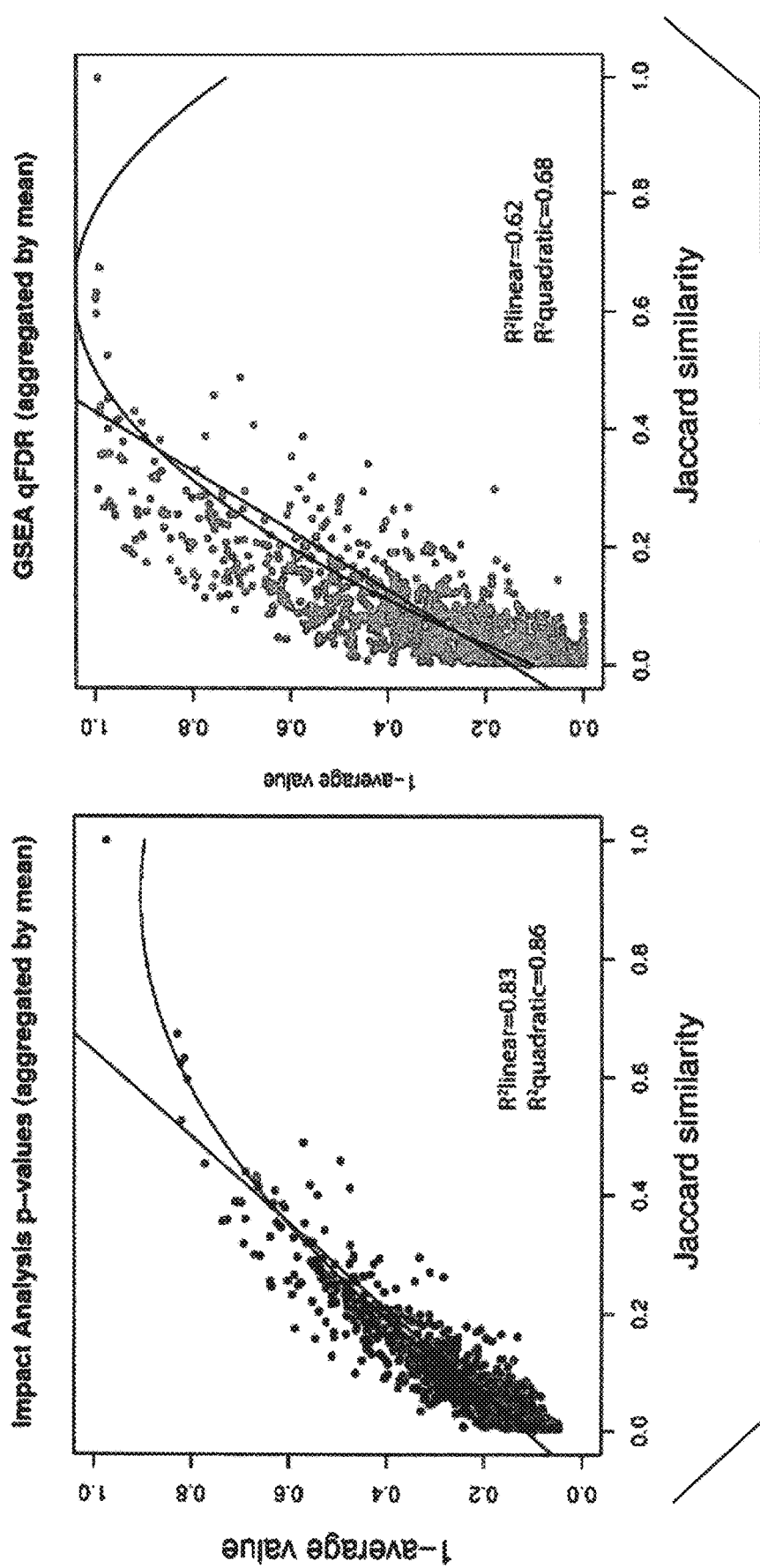

FIG. 12 are graphs showing the pathway coupling in the impact analysis (left panel) and GSEA (right panel). Each point represents the mean of all p-values of all random trials for pairs with the same Jaccard Index. The lines represent the fitting of linear and quadratic models. Both models show a strong dependence between the p-value coupling and the Jaccard Index.

Figure 13:
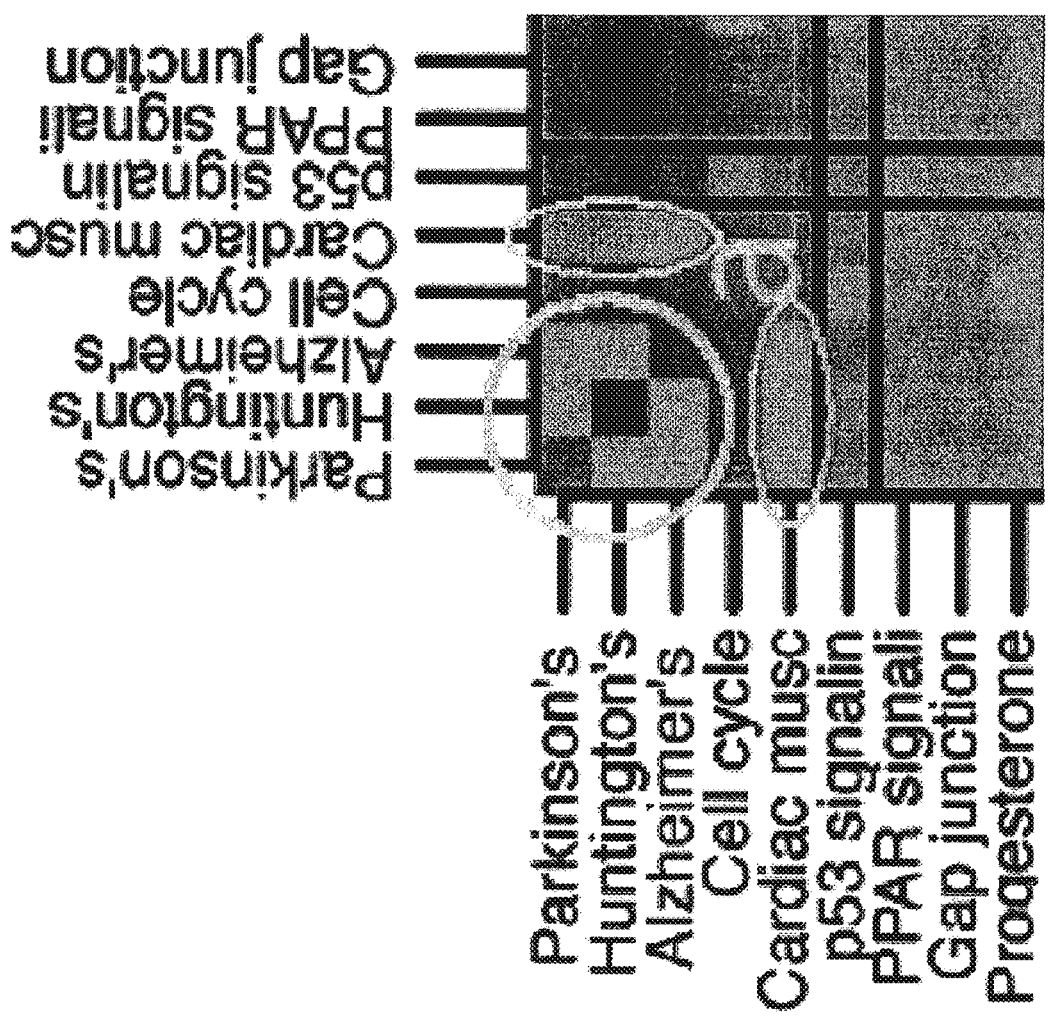

FIG. 13 is a detail of the crosstalk matrix for the comparison between days 7 and 0 in the same treatment. The areas marked with a correspond to the Mitochondrial activity pathway shown in FIG. 3, the same pathway that was found to be activated in the dataset associated with the comparison of expression levels at days 3 and 0.

FIGS. 14a and 14b show tabular results of the ORA for the fat remodeling experiment for the comparison between day 7 and day 0, with results "before" shown on the left (FIG. 14a) and "after" shown on the right (FIG. 14b). All p-values are FDR corrected. As depicted, in the "before" case on the left, the top 20 pathways resulting from classical ORA before correction for crosstalk. Four out of the top five pathways are not related to the fat remodeling phenomenon (false positives). As depicted in the "after" case on the right, the top 20 pathways after the correction for crosstalk effects. The mitochondrial activity pathway (validated in vivo) is reported as the most significant pathway even after 7 days, suggesting permanent tissue remodeling. The Phagosome pathway, significantly impacted after 3 days (see FIG. 1b) is not significant anymore after 7 days, consistent with the transitory nature of cellular death and phagocytosis. The four false positives in the left table have been removed. The ARVC is reported as a false positive but the DE genes located on this pathway are involved in cell adhesion which may be relevant here.

FIGS. 15a and 15b are tables depicting the results of ORA for the estrogen treatment experiment, before (left) and after (right) the correction for crosstalk effects. All p-values are FDR corrected. As illustrated in the "before" case (left), the top 20 pathways reported by the classical ORA before correction for crosstalk. The NSCLC, known to be linked to this treatment[15] is not identified by the classical method, while the SCLC, which showed no increase in incidence in the treatment group,[15] appears as significant. The significance of Pathways in Cancer is consistent with the putative link between hormone treatments and higher incidence of some types of cancer but offers no explanation or insight into the underlying mechanisms. As illustrated in the "after" case (right) the top 20 pathways reported by ORA after the correction for crosstalk effects. The correction method removed Pathways in Cancer, SCLC, and Prostate Cancer from the list of significant pathways, increasing the significance of pathways offering more insights such as Jak-STAT signaling pathway and the new Integrin mediated ECM signaling module. A star before the name of the pathway means that a module overlapping with other pathways has been removed from the pathway.

Figure 16:
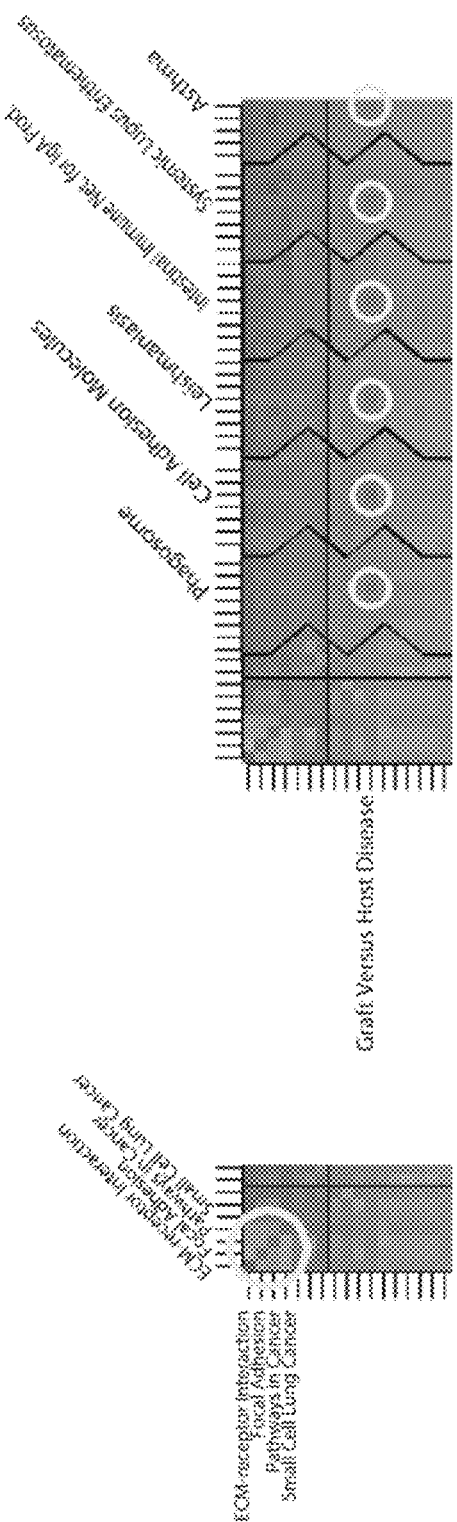

FIG. 16 provides a detail of the crosstalk matrix of the estrogen treatment. Left panel: the circle highlights an example of a common module that is responsible for the significance of an entire group of pathways. The common module between the pathways ECM-Receptor Interaction, Focal Adhesion, Pathways In Cancer, and Small Cell Lung Cancer describes the interaction between integrin and collagen, laminin, and fibronectin. Henceforth, we will refer to this module as the Integrin-mediated ECM signaling pathway (see FIG. 6). Right panel: row corresponding to the pathway Graft-Versus-Host disease. The pathway becomes significant after the removal of specific pathways, highlighted by the yellow circles. The set of pathways includes Phagosome, Cell adhesion molecules (CAMs), Leishmaniasis, Intestinal immune network for IgA production, Systemic Lupus Erithematosus, and Asthma. This indicates a situation in which the genes specific to Graft-Versus-Host disease are related to the phenomenon in analysis, but their significance is masked by the presence of crosstalk with other pathways.

Figure 17:
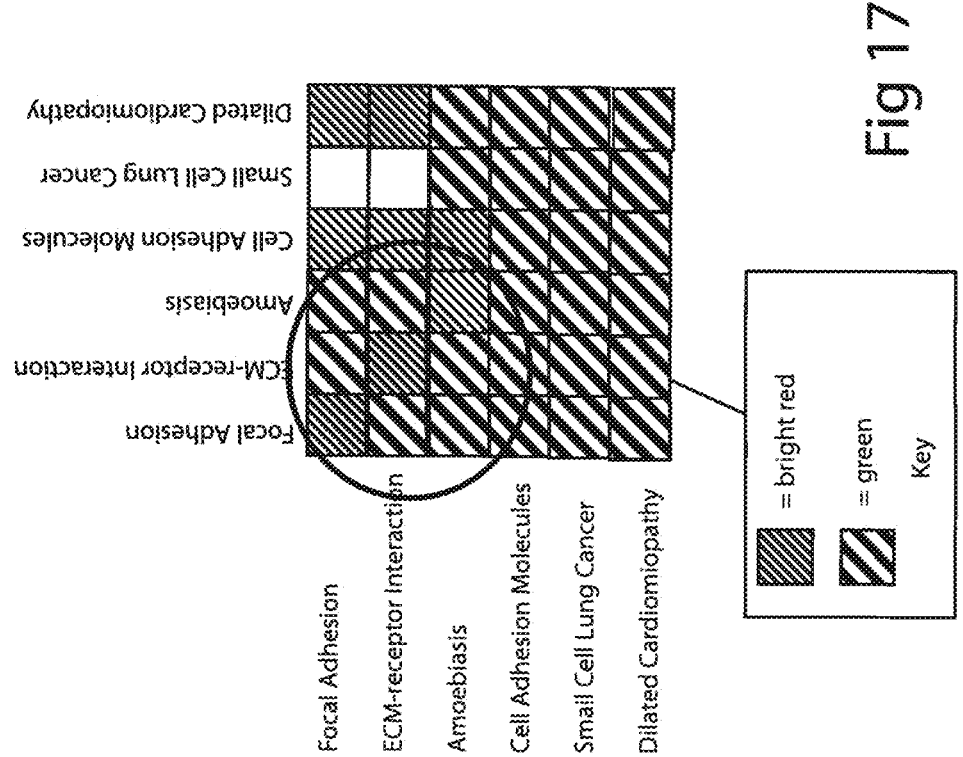

FIG. 17 provides details of the crosstalk matrix of the cervical ripening experiment. The circle highlights the evidence for an independent module involving pathways Focal Adhesion, ECM-Receptor Interaction, and Amoebiasis. This module is exactly the Integrin-mediated ECM signaling previously identified in the hormone treatment experiment (FIG. 6) from a different set of crosstalk interactions. The bright green loss of significance of Small-Cell Lung Cancer in columns 1-3, shows that this pathway was a false positive in the ORA since its significance was due only to the crosstalk from the first 3 pathways.

FIG. 18 is a table which provides an example of a DE/membership matrix; the column Y represents the indicator of differential expression of the various genes (1 for the n DE genes and 0 for the m NDE). Column $P_j$ represents the membership indicator for pathway j. Row gi describes gene i in terms of its differential expression and its membership to the various pathways.

Figure 19:
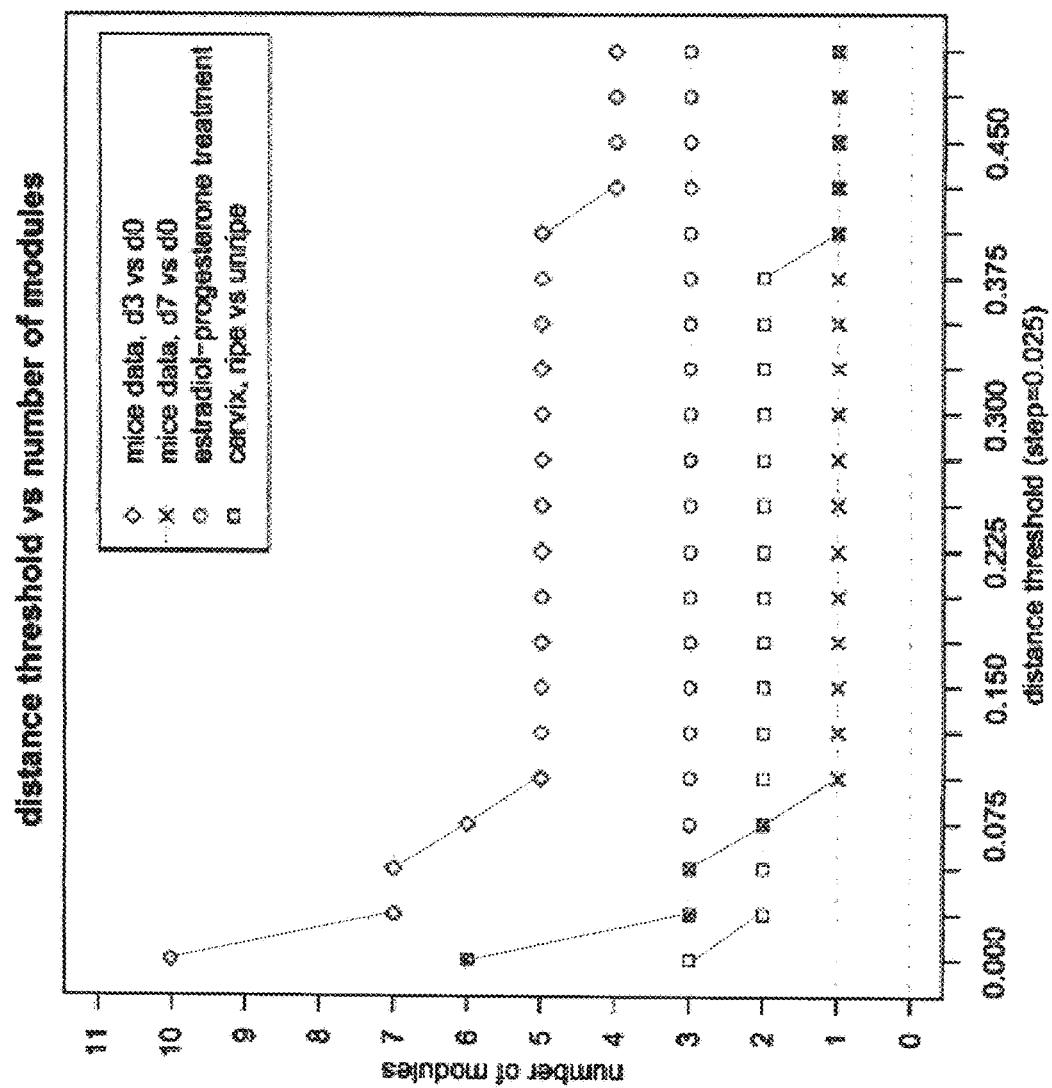

FIG. 19 is a graph depicting the number of modules obtained when changing the threshold distance under which two modules are considered similar enough to be joined. All data sets showed a plateau in the [0.1, 0.375] range indicating that the number of modules found does not depend on the choice of the threshold for a wide range of threshold values.

Figure 20:
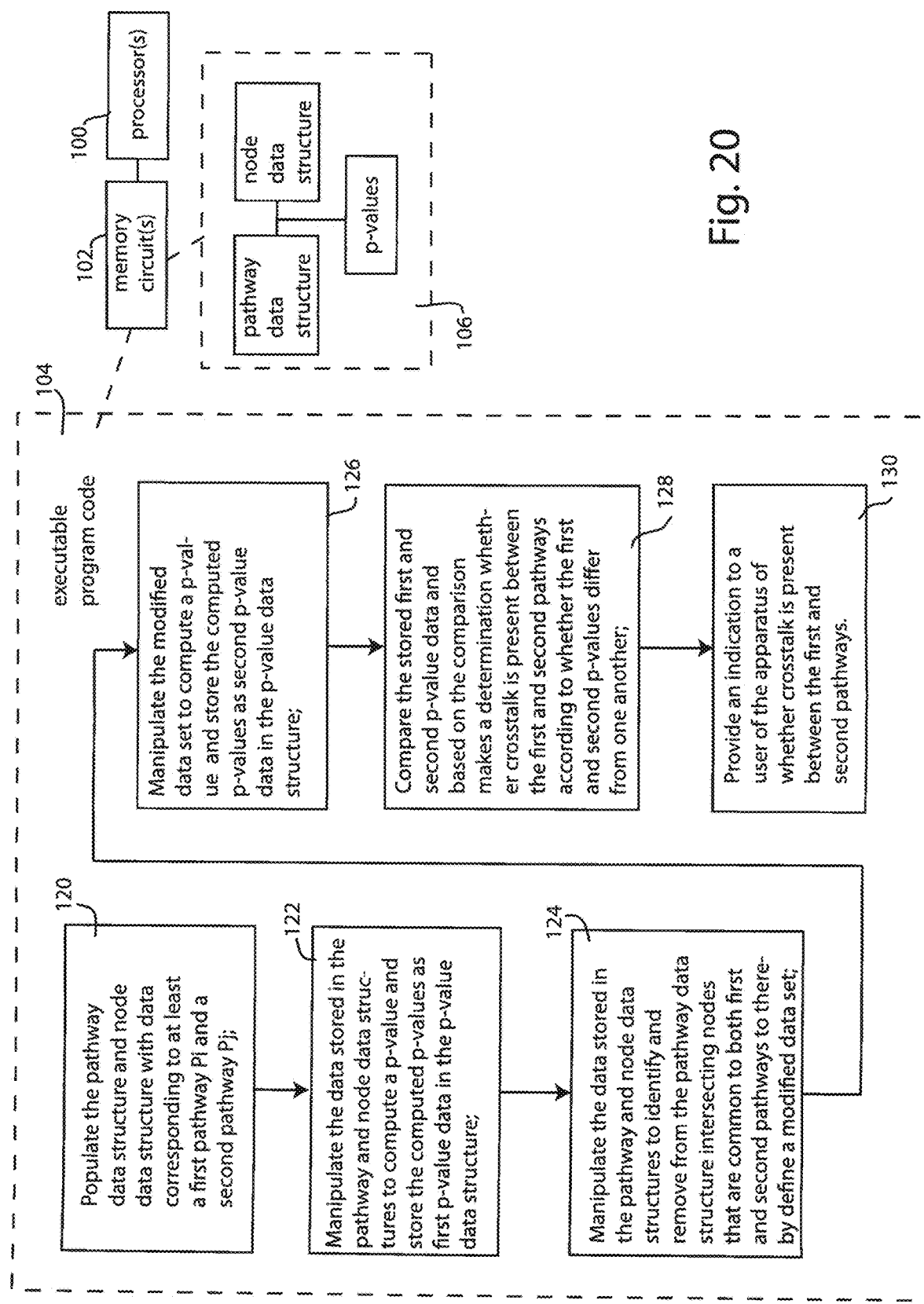

FIG. 20 is a computer-implementation diagram illustrating how the processor(s) and memory circuit(s) are configured to implement the described apparatuses and methods.

Corresponding reference numerals indicate corresponding parts throughout the several views of the drawings.

DETAILED DESCRIPTION

Example embodiments will now be described more fully with reference to the accompanying drawings.

Identifying pathways that are significantly impacted in a given condition is a crucial step in the understanding of the underlying biological phenomena. All approaches currently available for this purpose calculate a p-value that aims to quantify the significance of the involvement of each pathway in the given phenotype. These p-values were previously thought to be independent. Here, we show that this is not the case, and that pathways can affect each other's p-values through a "crosstalk" phenomenon that affects all major categories of existing methods. We describe a novel technique able to detect, quantify, and correct crosstalk effects, as well as identify novel independent functional modules. We assessed this technique on data from four real experiments coming from three phenotypes involving two species.

The correct identification of the signaling and metabolic pathways involved in a given phenotype is a crucial step in the interpretation of high-throughput genomic experiments. Most approaches currently available for this purpose treat the pathways as independent. In fact, pathways can affect each other's p-values through a phenomenon we refer to as crosstalk. Although it is intuitive that various pathways could influence each other, especially when they share genes, the presence and extent of this phenomenon have not been rigorously studied and, most importantly, there is no currently available technique able to quantify the amount of such crosstalk. There are three major categories of methods that aim to identify significant pathways: enrichment analysis (e.g. hypergeometric), functional scoring (e.g. GSEA), and topology-based methods (e.g. impact analysis). Here we show that the results of all these methods are affected by crosstalk effects, and that this phenomenon is related to the structure of the pathways. We propose the first approach that can: i) detect crosstalk when it exists, ii) quantify its magnitude, iii) correct for it, resulting in a more meaningful ranking among pathways in a specific biological condition, and iv) identify novel functional modules that can play an independent role and have different functions than the pathway they are currently located on. This method is expected to allow a better understanding of individual experiment results, as well as a more refined definition of the existing signaling pathways for specific phenotypes.

Crosstalk Effects

In order to demonstrate the existence and assess the extent of crosstalk effects, we conducted a systematic exploration of this phenomenon. We constructed a reference set of genes from all genes present in at least one KEGG signaling pathway (2,963 genes at the time). Then, each pathway was used as a "bait", choosing from it a number of genes that would make it significant at a chosen significance level ($\alpha=0.01$ after Bonferroni correction). Other random genes were selected up to a constant number (n=100) of "differentially expressed" (DE) genes (details discussed below). Under these circumstances, the research hypothesis is true for the bait, while the null hypothesis is true for all other pathways. We repeated this selection 1,000 times for each pathway Pi, and each time we computed the hypergeometric,[1] SPIA (impact analysis), and GSEA p-values for all pathways from the KEGG database.[7] With these results, we constructed the empirical distributions of the False Discovery Rate (FDR)-corrected p-values corresponding to each prey Pj. The distributions of the p-values for all three methods are severely skewed towards zero, showing that all methods produce a significant number of false positives due to crosstalk effects (FIG. 10). We hypothesized that crosstalk is mostly due to the common gene between pathways. If this were true, we would expect to see a strong coupling between pairs of pathways with many genes in common and a weak coupling between pathways that do not share any genes. In order to test this hypothesis, we calculated the Jaccard similarity index for each pair of pathways, as well as the Pearson correlation between the Jaccard index and the p-values of the preys (FIGS. 11 and 12). The data shows a very strong correlation (Pearson correlation index of 0.87 for hypergeometric, 0.62 for GSEA and 0.83 for SPIA), which confirms our hypothesis that the crosstalk can be explained by the presence of "busy" genes, i.e. genes that are involved in more than one pathway.

Results

Crosstalk analysis and correction. The method we propose for correcting for crosstalk effects takes as input a set of reference pathways and a list of genes that are DE in the given condition. The crosstalk analysis is composed of three steps. The first step is the computation of a crosstalk matrix, i.e. the analysis of pairwise crosstalk interactions between pathways in the given condition, resulting in a heat map showing the p-value of each pathway when the genes from each other pathway are removed. This matrix allows the visualization of various cases of crosstalk effects and provides information on the extent of crosstalk effects in the condition analyzed. The second step is the module detection that allows the identification of sub-pathways that appear to be involved in the specific condition studied independently of the pathway they belong to. The final step is the maximum impact estimation, where the biological impact of each gene is assigned to only one of the pathways to which the gene belongs, for those genes that belong to more than one pathway. The result of the last two steps is essentially a new set of pathways that can include: a) original pathways as found in the literature, b) novel functional modules that might be relevant to the given condition, and c) pathways modified by the removal of a such a functional module. The new set of pathways is not affected by crosstalk effects, and new p-values are computed for each pathway, building a ranked list from which the false positives due to crosstalk have been removed (see Materials and Methods below).

Fat remodeling in mice. We include here the results of the crosstalk analysis in an experiment investigating cellular and metabolic plasticity of white fat tissue (WAT), where the classical overrepresentation analysis (ORA) produced a number of false positives, and failed to rank highly pathways that were known to be involved in the given condition. In this experiment, the chronic activation of WAT β-adrenergic receptors by certain physiological and pharmacological conditions transforms the tissue into one resembling brown fat, a thermogenic organ. The data set was obtained from a microarray analysis of white fat from mice treated with low dose (0.75 nmol/hr) CL 316,243 (CL) for 0, 3 and 7 days. Here we discuss only the list of DE genes coming from the comparison between expression levels of genes at days 3 and 0 (for the comparison between days 7 and 0, see discussion below).

The top 20 pathways ranked by ORA and their associated FDR-corrected p-values are shown in FIG. 1a. The three most significant pathways in the comparison between days 3 and 0 were Parkinson's, Alzheimer's and Huntington's diseases. The fourth pathway in the ranked list is Leishmaniasis. The first three pathways describe degenerative diseases of the central nervous system which have no connection to fat remodeling. Leishmaniasis describes the signaling involved in a disease spread by the bite of certain species of sand flies. Clearly, this pathway is also unlikely to give insights about the fat remodeling phenomenon. While other pathways such as Phagosome, PPAR Signaling, and Cell cycle, are definitely more related to the phenomenon of fat remodeling, their presence in the middle of a ranked list dominated by false positives (6 false positives in the 10 pathways significant at 1%) illustrates how the crosstalk effects make the classical ORA unable to find the truly relevant pathways.

Figure 2:
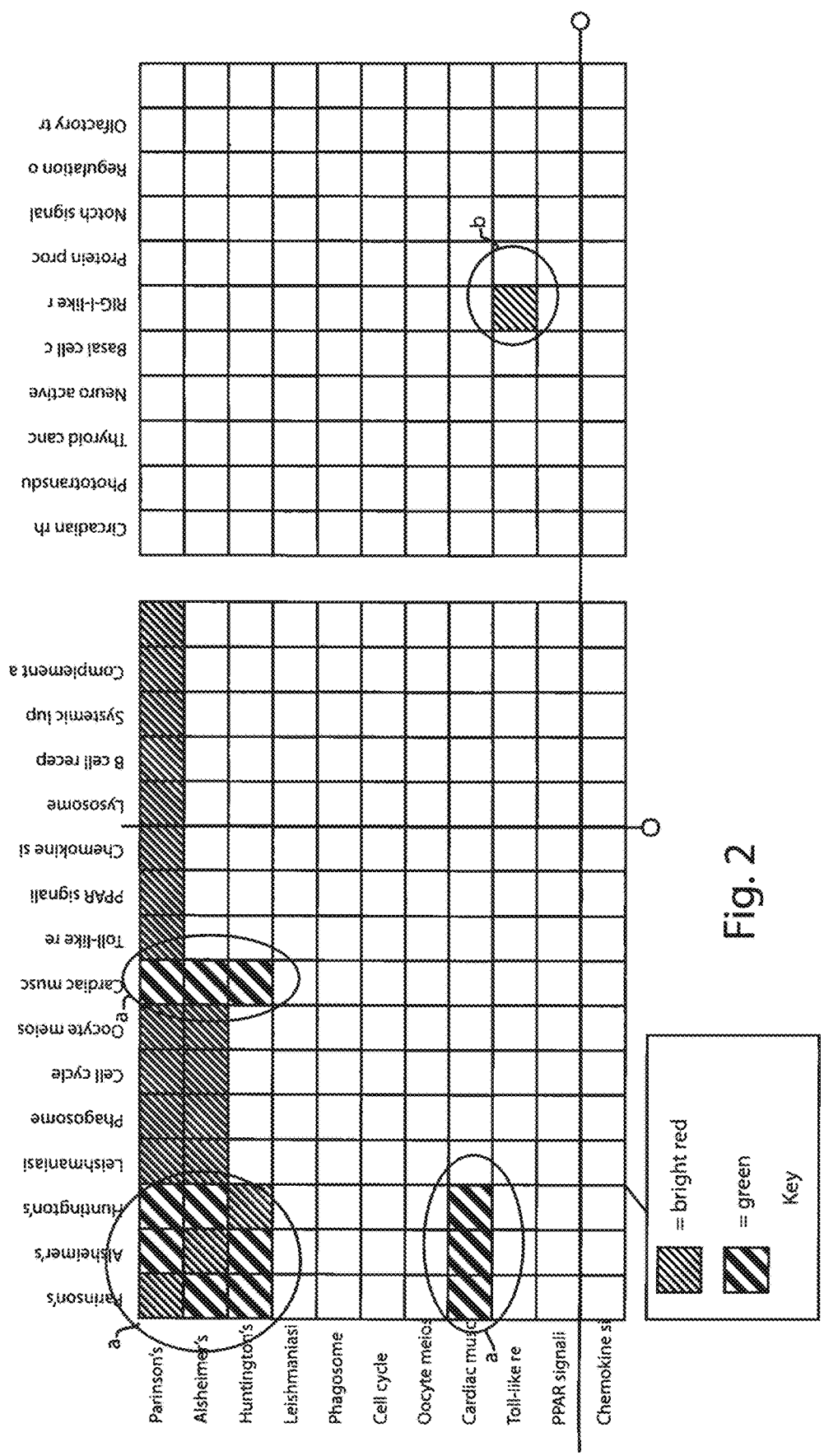
FIG. 2 is a crosstalk matrix "heat map" diagram comparing day 3 and day 0 in the CL treatment.

In order to analyze and eliminate the crosstalk effects we computed the crosstalk matrix as described in the Methods section. The analysis of the matrix illustrates some interesting examples of crosstalk effects. FIG. 2 represents a detail of the entire matrix. If desired the matrix may be generated using different colors to depict different significance levels. In the exemplary illustration of FIG. 2 crosshatched patterns have been used instead of colors, to support a black & white representation for Patent Office convenience. Some "colors" have been suppressed in FIG. 2 to simplify the explanation. In this figure, the high significance of Parkinson's (bright red in row 1, column 1—see Key for color designators) disappears when the crosstalk due to Alzheimer's is eliminated (green in row 1, column 2—see Key for color designators). This indicates that Parkinson's is a false positive, since its significance is due exclusively to genes from Alzheimer's. Furthermore, the high significance of Alzheimer's (bright red in row 2, column 2) also disappears when the crosstalk effect of Parkinson's is eliminated (green in row 2, column 1). This means that Alzheimer's significance is also due only to the genes in common with Parkinson's. Essentially, the analysis tells us that the genes in common between the two pathways are activated independently of either pathway, which suggests that these genes constitute an independent functional module. The same phenomenon involves the Cardiac Muscle Contraction and Huntington's disease pathways. The same independent functional module is responsible for the changes shown in areas marked with a in FIG. 2.

Figure 3:
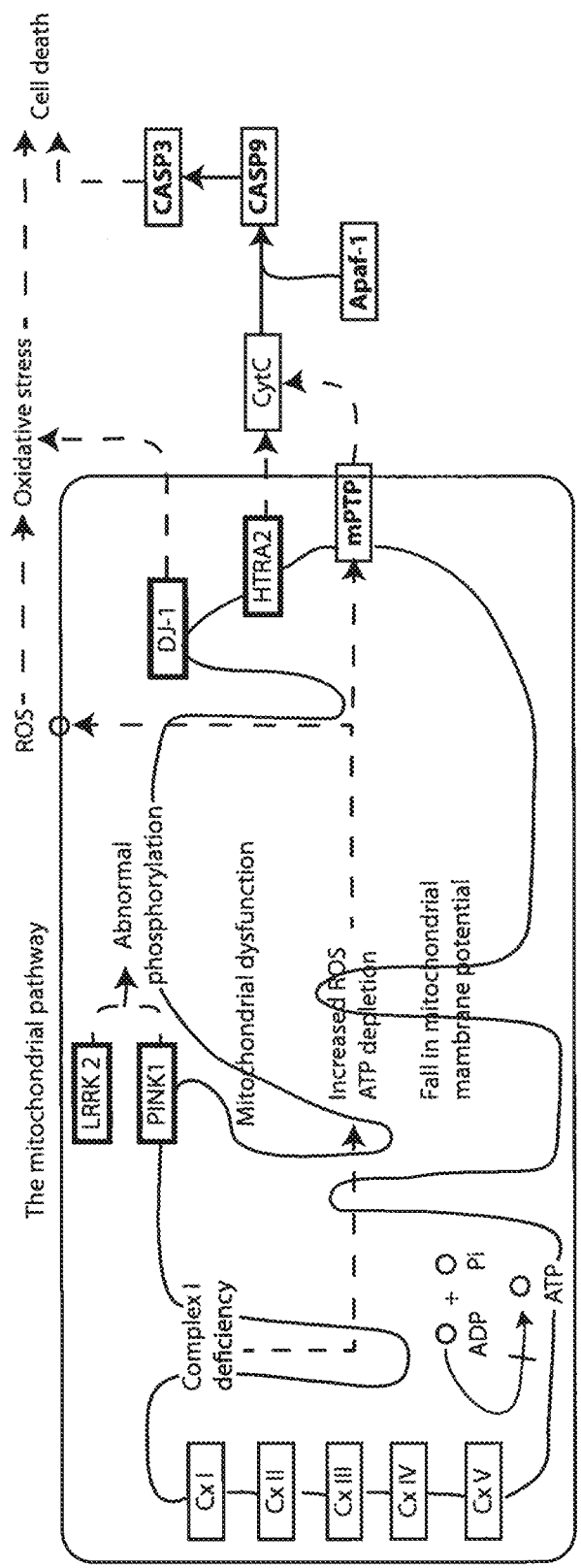
FIG. 3 illustrates the mitochondrial activity pathway, an independent functional module responsible for incorrect identification of the pathways Parkinson's disease, Alzheimer's disease, Huntington's disease and Cardiac Muscle Contraction by classical ORA.

An inspection of these genes and their signaling mechanisms reveals that this module is composed by genes present in mitochondria, organelles involved in all pathways above. The fact that this module is strongly activated in this fat remodeling experiment that is not related to any of the above conditions (Alzheimer's, Parkinson's, Huntington's), suggests that this should be considered as an independent pathway, dedicated to mitochondrial activity. FIG. 3 shows a representation of this new pathway.

FIG. 4 shows a comparison between the control (left) and CL-treated mice (right). The right panel of this figure shows a massive generation of new mitochondria after 7 days of treatment, demonstrating in vivo that indeed, the mitochondrial pathway is central in this experiment.

Another very interesting phenomenon can be observed in FIG. 2 (circle b). Here, Toll-like Receptor Signaling (TLR) pathway becomes more significant when the Rig-I Like Receptor Signaling (RLR) pathway (not significant on its own) is removed. The TLR pathway is the generic pathway involved in the immune response. The RLR pathway is the antiviral innate immunity pathway, which includes the mechanisms specifically aimed at the detection of exogenous DNA or RNA. In essence, the crosstalk analysis tells us that in the fat remodeling experiment, the immune system has been activated but this immune response is not due to the presence of foreign genetic material. This is exactly what happens here. The CL treatment causes the death of some white fat cells. In turn, this causes an immune response in which macrophages are required to dispose of the dead cells. Such subtle distinctions between various triggers that activated the immune response are not possible with any classical analysis methods, and it is remarkable that a data analysis method was able to provide this type of insight.

We then applied the proposed Maximum Impact Estimation described in the Methods section to the data. The corrected p-values are shown in FIG. 1b. The ranking based on these crosstalk corrected p-values is greatly improved. The most significant pathway is now the newly discovered mitochondrial pathway shown in FIG. 3 and validated by the in-situ hybridization shown in FIG. 4. The new p-values also indicate the Phagosome pathway as one of the pathways related to this phenomenon. Third in the list is an independent module shared by Cell Cycle and Oocyte Meiosis. This can be thought of as a pathway related to the creation of new cells. Finally, the true involvement of PPAR signaling pathway in the phenomenon of fat remodeling has been previously demonstrated. After removing the influence of the mitochondrial crosstalk, the Parkinson's, Alzheimer's, and Huntington's pathways are not significant anymore (now ranked $60^{th}$, $61^{st}$ and $54^{th}$, respectively, data not shown). Also, after removing the crosstalk from Phagosome, Leishmaniasis is not significant anymore (now ranked $62^{nd}$, data not shown).

Cervical ripening. The second dataset analyzed was obtained from a recent study that investigated the transcriptome of uterine cervical ripening inhuman pregnancy before the onset of labor at term. The tissue analyzed is the human uterine cervix, the lower part of the uterus extending from the isthmus of the uterus into the vagina. It is mainly composed of smooth muscle and extracellular matrix, which consists of collagen, elastin, proteoglycans, and glycoproteins. The uterine cervix has an essential function in the maintenance of pregnancy and also in parturition. Cervical ripening is a critical component of the common terminal pathway of parturition, which includes the extensive remodeling of the cervix. Disorders of cervical ripening can lead to premature or protracted cervical change, complicating term (e.g. protracted dilatation or arrest of dilatation) or preterm gestations (e.g. premature cervical dilation in the second trimester).

The state of cervical ripening has traditionally been assessed by clinical examination (Bishop score or its modifications), which includes the digital examination of the cervix for its consistency, dilatation, effacement, and position. This method has also been used to predict the likelihood that a patient would go into spontaneous labor. The goal of this experiment was to examine the relationship between human cervical ripening and the cervical transcriptome, aiming to improve our understanding of the biology of cervical ripening at term. This study included pregnant women who underwent elective C-section at term with an unripe (n=11) or ripe cervix (n=11). Cervical biopsies were obtained from these women transvaginally, from the anterior lip of the uterine cervix following C-section. Microarray analysis was performed on RNA isolated from these cervical tissue specimens using Affymetrix GeneChip HGU133Plus2.0 arrays.

On the same dataset we performed the comparison between gene expression levels from cervical tissues obtained from women with an unripe (n=11) or ripe cervix (n=11) using the classical ORA. The results are shown in FIG. 5a. Pathways with a p-value smaller than 0.05 after FDR correction were Focal adhesion, ECM-receptor interaction, Amoebiasis, Cell adhesion molecules (CAMs), Small cell lung cancer, and Dilated cardiomyopathy.

There is plenty of experimental evidence that biological processes described by the pathways Focal Adhesion, ECM-Receptor Interaction, and Cell Adhesion Molecules are related to cervical ripening. The relation between these pathways and the phenomenon in analysis was revealed by studies on humans and animals showing the involvement of extra-cellular matrix metabolism and cell adhesion molecules in cervical ripening. However, the pathway Amoebiasis describes the biological process of infection from a parasite that invades the intestinal epithelium. Amoeba infection involves the parasite attachment to the intestinal mucus layer, followed by disruption and death of host epithelial cells. This process is completely unrelated to the physiological condition of cervical ripening in term pregnancy. The same is true for the Small Cell Lung Cancer pathway. Clearly, the top ranked pathways include some describing complex phenomena that are unrelated to the studied condition. Also, the significant pathways known to be involved in the process of cervical ripening are somewhat general pathways describing cellular interactions.

The analysis of the crosstalk matrix (see FIG. 17) shows that there is an independent functional module among the top three pathways in the ranking. This novel module includes the genes present in the interaction between the cellular transmembrane protein integrin and three important ECM components, collagen, laminin, and fibronectin. The KEGG pathways involved in the identification of this pathway are Focal adhesion, ECM-receptor interaction, and Amoebiasis. Henceforth, we will refer to this pathway as the Integrin-Mediated ECM Signaling (FIG. 6).

Very interestingly, the independent functional module found in this condition is, in fact, the exact same module found in the hormone treatment experiment described below. Interestingly, the KEGG pathways involved in the identification of this functional module are slightly different between the two phenotypes. While in this phenotype this module was found from the interaction of Focal adhesion, ECM-receptor interaction and Amoebiasis, in the hormone treatment the last pathway is replaced by Pathways in Cancer. The fact that the same module was found to be activated and statistically significant in two different phenotypes, from the interaction of different sets of canonical pathways, further supports the idea that this module describes an independent mechanism and should therefore be considered as an independent pathway.

Further analysis of the crosstalk matrix shows that the Small Cell Lung Cancer loses significance when the crosstalk effects of the first three pathways are removed (bright green loss of significance in first 3 columns of row 5 in FIG. 17). This allows us to conclude that it is a false positive in the classical ORA, with its ORA significance due exclusively to crosstalk effects.

The ranking of pathways after applying our analysis is shown in FIG. 5b. The first pathway is Integrin-mediated ECM Signaling with an FDR corrected p-value of $2.9e^{-13}$. Cell Adhesion Molecules is now the second in ranking, with an FDR corrected p-value of 0.004. The false positives in the classical ORA results, Amoebiasis and Small Cell Lung Cancer, are not significant anymore. The biological significance of the pathway Dilated Cardiomyopathy may be linked to the fact that 10° lo-15° lo of the uterine cervix is constituted of smooth muscle, and cervical ripening involves alterations of this component. The last significant pathway at the 5° lo significance threshold is Leukocyte Transendothelial Migration. Although human and animal studies have shown that cervical ripening does not require activation of a typical inflammatory response, and influx of inflammatory cells into the cervix, the significance of this pathway may reflect the beginning of later inflammatory events typical of parturition.

In addition to these data sets, we analyzed another data set coming from the comparison of expression levels at days 7 and 0 in the fat remodeling experiment (see the Supplementary Results section below), as well as a data set investigating the effect of various types of hormones on the endometrium of healthy post-menopausal women who underwent hysterectomy. This approach was able to eliminate most false positives, as well as correctly identify as significant pathways that had been biologically proven to be involved in the given condition, yet not found to be significant by the classical analysis. We also found several independent functional modules including a mitochondrial activity module active in a different stage of fat remodeling, and an integrin-mediated ECM signaling found to be involved in hormone treatment in post-menopausal women and cervical ripening. Interesting, the later module was extracted independently from the crosstalk interactions of two different groups of pathways, in the two conditions analyzed.

CONCLUSIONS

These results show that our method for the detection and correction for crosstalk effects allows not only the elimination of most of the false positives present in the results of the classical ORA, but also the identification of novel functional sub-pathways that are specifically involved in the condition studied, giving useful insights on the phenomenon in analysis that are not captured by existing techniques. This is a departure from the current paradigm that considers the pathways as static models, independent of the phenotype. In the view proposed here, various specific modules, or sub-pathways, can be dynamically linked to specific conditions. When such independent functional modules are identified in independent conditions, such as the integrin-mediated ECM signaling above, these modules could be considered as candidate new pathways.

Online Methods

Pathway analysis in the presence of overlapping pathways: the crosstalk matrix. Our goal is to develop an approach that can detect and quantify the crosstalk between pathways. The main issue we are trying to address here is the fact that in the presence of overlapping pathways (i.e. for all pathways databases available today) crosstalk phenomena increase the probability of false positives, i.e. increase the number of pathways reported as significant but that in reality are not interesting (borrowing terminology from Brad Efron, we call pathways that have lesser biological significance "not interesting" even though they might be statistically significant with a large enough sample size).

To better understand the approach we are going to present, let us briefly review the classical hypergeometric approach described above. FIG. 7a represents the contingency table used for assessing the significance of a pathway $P_i$ by the classical ORA approach. The table divides genes as either being in the pathway or not, versus being considered DE or not DE (NDE); $n_i$ represents the number of DE genes on $P_i$, while n represents the total number of DE genes, and $m_1$ represents the number of NDE genes on $P_z$ while m represents the total number of NDE genes. It follows that $n_i+m_i=|P_i|$ represents the number of genes on $P_i$, while with n+m we represent the total number of genes.

The reasoning behind the over-representation (ORA) analysis is that if the number of DE genes on a pathway is much higher than expected by chance, then the pathway is likely to be biologically interesting. In order to take into account the effect of the overlap on the significance of the two pathways we consider the effect of the removal of the overlapping part on the significance of the pathways. This is achieved as follows: let us consider two overlapping pathways $P_i$ and $P_j$. With the notation $P_{i\backslash j}$ we define the set of elements in $P_1$ excluding the intersection with $P_j$; in the same way, with the notations $n_{i\backslash j}+m_{i\backslash j}$ we represent the number of genes that are in pathway $P_i$ but not in pathway $P_j$, and with $n_{i\backslash j}$ the number of DE genes that are on pathway $P_i$ but not in pathway $P_j$. We then consider the contingency table shown in FIG. 7b, whose bottom margin is identical to that of FIG. 7a.

With this contingency table, we compute for every pair of pathways [i,j] the p-value of $P_{i\backslash j}$. Since this computation yields an k×k matrix, where k is the number of pathways, the results are most conveniently represented using a heat map of the negative log p-values. Each cell (i,j) of this matrix characterizes the significance of pathway $P_i$ when we remove the effect of pathway $P_j$. The rows and the columns are ordered by the original p-values of the pathways, which are placed on the diagonal. We will refer to this matrix as the crosstalk matrix. This matrix is useful for identifying the effects of crosstalk among pathways.

An example of the crosstalk matrix can be found in FIG. 8. We will refer to the part of the matrix above the horizontal significance threshold as the significance strip. The non-significance strip will be the part below the horizontal significance threshold. The significance quadrant will be the part of the significance strip to the left of the significance threshold. Using these terms, we can identify and discuss several interesting phenomena that are not captured by any of the existing pathway analysis methods.

A first interesting case is when a pathway $P_i$ is reported as significant by the classical analysis, but it loses its significance when the effect of another pathway $P_j$ is removed. This is represented, in the crosstalk matrix, by a non-significant p-value (green square) in the significance strip. In this case $P_i$ is unlikely to be biologically meaningful, since its significance is most likely due to a crosstalk from $P_j$.

A second interesting case is when a pathway $P_1$ that is not significant for the classical analysis becomes significant when the crosstalk effect of another pathway $P_j$ is removed. This is represented in the crosstalk matrix by a significant p-value (red square) in the non-significant strip. The meaning of this is that pathway $P_j$ was masking the significance of $P_i$, indicating that a phenomenon likely to be biologically meaningful is happening in the part of $P_i$ which is not in common with $P_j$.

A third and last interesting case is a symmetric (with respect to the diagonal) decrease in significance of pathways in the significance quadrant. This indicates the presence of an independent functional sub-module, common to both $P_i$ and $P_j$, that is responsible for their significance. Note that the activity of this module is tightly related to the condition studied.

The maximum impact estimation: an expectation maximization technique for the assessment of the significance of signaling pathways in presence of crosstalk. The crosstalk matrix is a useful tool for the interpretation of the effect of crosstalk between pathways. However, the ultimate goal of the analysis of signaling pathways is to provide a meaningful ranking among pathways, as well as a p-value quantifying the likelihood that a certain pathway is involved in the phenomenon in analysis. Here, we developed a correction method for the ranking of pathways that takes in account the overlaps between pathways.

The main idea is that, if there is no crosstalk, then there is no ambiguity in the ORA significance calculations. In such a case, if genes in a path are over-represented, it cannot be a false positive caused by crosstalk. Our approach is therefore to infer an underlying pathway impact matrix where each gene contributes to one and only one pathway, hence is devoid of crosstalk, and then to perform the ORA analysis using that impact matrix. Since this underlying pathway impact matrix is not observed directly, it is inferred through likelihood-based methods, and estimated using the EM algorithm. The corrected ranking is computed using ORA analysis with the underlying pathway impact matrix, shown as follows.

Let us consider the DE indicator vector Y, representing the differential expression of genes, and the membership matrix X describing the membership of each gene in each one of k pathways $P_1 \ldots P_k$. The vector Y is defined as follows:

$$Y_i = \begin{cases} 1 & \text{if } g_i \text{ is } DE \\ 0 & \text{if } g_i \text{ is } NDE \end{cases}$$

and each cell $X_{i,j}$ of the matrix X is defined as follows:

$$X_{ij} = \begin{cases} 1 & \text{if } g_i \text{ belongs to } P_j \\ 0 & \text{if } g_i \text{ does not belong to } P_j \end{cases}$$

The matrix Y|X obtained by combining the vector Y with the X matrix is shown in the example in FIG. 9.

In many analysis methods, the membership matrix X is also interpreted as the impact matrix: if $X_{ij}=1$, then gene gi impacts pathway $P_j$. In ORA, for example, each gene is considered to have the same full impact on all pathways the gene belongs to. Crosstalk effects result from the fact that a gene can belong to more than one pathway, but in principle, it can potentially have a different biological impact on each such pathway. Our aim is to identify the pathway where the biological impact of such a shared gene is maximum. We do so by estimating the maximum impact pathway using an expectation maximization approach (see discussion below).

Identification of independent functional modules. The maximum impact estimation procedure alone is not be able to identify overlapping modules responsible for the entire significance of other pathways, as in the situations represented by case 3 in the section describing the crosstalk matrix. In such cases the overlap should be considered as a separate pathway that is more likely to be biologically meaningful in the condition under analysis. An additional step is needed in order to correctly deal with this situation. In this additional step, we extract certain significant overlaps from the list of pathways, and include them in the list as independent functional modules. An independent functional module is a module for which there is evidence of an activity independent of the pathways it resides in, for the given condition. If an independent module is found in more than one, possibly unrelated, conditions, this module is considered as a candidate novel pathway.

A module must satisfy certain conditions in order to be treated as an independent functional module. Let us assume that we are analyzing the overlap between the pathways $P_i$ and $P_j$; the first condition is that both pathways are significant (after correction for multiple comparisons) at a certain threshold $\alpha$. This condition limits the search to the significance quadrant of the crosstalk matrix. The second condition is that the overlap $P_{i \cap j}$ itself must be significant at $\alpha$. The third condition is that the sub-pathways obtained by removing the overlap from both original pathways, indicated by $P_{i \backslash j}$ and $P_{j \backslash i}$ must not be significant at $\alpha$. If we denote with p(P) the p-value of a generic pathway P, then the conditions can be summarized as follows:

$$p(P_i)<\alpha, p(P_j)<\alpha \qquad (1.)$$

$$p(P_{i \cap j})<\alpha \qquad (2.)$$

$$p(P_{i \backslash j}) \geq \alpha, p(P_{j \backslash i}) \geq \alpha \qquad (3.)$$

This pairwise procedure might yield modules that are similar one to each other, for example in cases where a module is contained in three or more pathways. That could be solved with a three-way or n-way search, but we opted for another approach for limiting the number of new modules. Once all interesting pairwise modules are created, we test for similarity among modules. The index used for similarity is a modified Jaccard Similarity index mJS defined as follows:

$$mJS = \frac{|M_1 \cap M_2|}{\min(|M_1|, |M_2|)} \qquad (1)$$

where $M_1$ and $M_2$ are two modules obtained with the search criteria explained above. We merge any two modules similarity is greater that a certain threshold st. Once the modules are merged, the similarity among all the modules (including the newly created one) is computed again, and the merging procedure is applied again until there are no more modules that can be merged.

This newly created modules are removed from all pathways with which they overlap, and this list of modified pathways is used in the EM procedure. For the data sets analyzed in this work, we used a threshold of 0.25. The motivation for the selection of this threshold is discussed below.

After applying the module discovery and the EM approach, the result is a modified membership matrix that can be used to perform the desired type of analysis. This matrix now includes three types of pathways: i) original pathways as found in the literature, ii) novel functional modules that are impacted in the given condition independently from the pathways they belong to, and iii) the pathways from which such independent modules have been removed. If the same independent module is found in several conditions, in other words if this module is active independently from its parent pathways in several different phenotypes, such a module should be considered a good candidate for a novel pathway.

Crosstalk Phenomena

We hypothesized that pathways can consistently affect each other's p-values in significant ways through crosstalk. Identifying such effects in any number of specific real experiments would constitute only anecdotal evidence since the true amount of crosstalk between two given pathways in any given condition is not known. In order to demonstrate the existence and assess the extent of crosstalk effects, we designed and conducted the following systematic exploration of this phenomenon. We first constructed a reference set of genes from the union of all genes present on at least one KEGG signaling pathway (2963 genes at the time). Then, for each pathway $P_i$, we ran experiments as follows. We first calculated the number $n_i$ of DE genes that would make $P_i$ significant at least at $\alpha=0.01$ after a Bonferroni correction for multiple comparison. Henceforth, we will refer to this pathway as the "bait". We then used the reference set to pick $n_i$ random genes from $P_i$ and 100–$n_i$ genes that are not on $P_i$, and calculated the hypergeometric significance of all other "prey" pathways, $P_j$. This essentially models a situation in which 100 genes are found to be DE, and these genes are such that the hypergeometric analysis will find the bait pathway $P_i$ significant at 1% after the correction for multiple comparisons. Since the 100–$n_i$ genes that are not on $P_i$ are randomly chosen among the reference set, no other pathway $P_j$ should have more genes than expected by chance. Under these circumstances, the research hypothesis is true for the bait, while the null hypothesis is true for all other pathways. We repeated this selection 1,000 times for each pathway $P_i$, and each time we computed the hypergeometric, SPIA (impact analysis), and GSEA p-values for all pathways in the set S including all the pathways from KEGG. With these results, we constructed the distributions of the FDR-corrected p-values corresponding to each prey $P_j$. Under the null hypothesis, the p-values are expected to follow an uniform distribution, and to be independent between different pathways. In fact, the distributions of the p-values (see FIGS. 10a, 10b and 10c) are significantly different from the uniform distribution (Kolmogorov-Smirnov goodness of fit p-values of the order of $10^{-16}$ in all cases). The distributions for all three methods are severely skewed towards zero, showing that all methods produce a large number of false positives.

Furthermore, we observed much stronger crosstalk effects for specific pathway pairs (i,j): every time one of them is used as a bait, the p-value of the other one is pulled to values much lower than expected by chance, many times well below the significance threshold. All crosstalk effects can be represented in a crosstalk matrix (left panel in FIG. 11). In this matrix, the elements[i,j] represent the mean of the distribution of p-values for 1,000 random trials using pathway i as bait and pathway j as prey. This matrix is not symmetrical since the influence of pathway i on pathway j can be different from the influence of pathway j on i. The matrix shows strong crosstalk between several pathways (e.g. row 3 and columns 57 through 70).

We hypothesized that this crosstalk is due mostly to the genes that are in common between pathways. If this were true, we would expect to see a strong coupling between pairs of pathways that have many genes in common and a weak coupling between pathways that do not share any genes. In order to test this hypothesis, we calculated the Jaccard similarity index between all pairs of signaling pathways from KEGG. The Jaccard index is defined as $$\frac{|P_i \cap P_j|}{|P_i \cup P_j|}$$

and characterizes the overlap between two sets, relatively to the size of their union. Pathways that share many genes will have a large Jaccard index. The right panel in FIG. 11 shows the relationship between the hypergeometric p-values and the Jaccard index for all pathway pairs. The data shows a very strong correlation between the two (Pearson correlation index of 0.87), which confirms our hypothesis that the crosstalk can be explained by the presence of "busy" genes, i.e. genes that are involved in more than one pathway. Very similar results have been obtained for FCS analysis (GSEA) and for the impact analysis (SPIA) (see FIG. 12). The Pearson correlation between the p-values provided by GSEA and the Jaccard indices of all KEGG pathways was 0.62, while in the case of SPIA the correlation was 0.83.

Supplementary Results

Fat remodeling in mice. The first additional results to be discussed here were obtained from the comparison between expression levels of genes at days 7 and 0 in the same fat remodeling experiment discussed in the main article. The genes were ordered by p-values and the top 5% were selected as differentially expressed (DE). The results of the classical ORA are shown in FIG. 14a) (only the top 20 pathways are shown). The top pathways are Parkinson's disease, Alzheimer's disease, and Huntington's disease, diseases that have little to do with the tissue remodeling phenomenon. The Cell Cycle pathway is likely to be related to tissue remodeling, and p53 Signaling is known to be a central pathway in the response to cellular stress, including inflammation, and related to processes like cellular senescence and cell cycle. With four false positives in the top five pathways, the results of the classical ORA are distorted by pathway crosstalk phenomena to the point of being useless.

In order to identify and eliminate the crosstalk effects we computed the crosstalk matrix described in the Materials and Methods section. FIG. 13 represents a detail of the entire matrix.

The areas marked with a highlight the same phenomenon present in the matrix corresponding to the comparison between days 3 and 0 of the same experiment. The significance of the pathways Parkinson's disease, Huntington's disease, Alzheimer's disease, and Cardiac Muscle Contraction is entirely due to the same mitochondrial activity pathway shown in FIG. 3 in the main text. The greatly enhanced mitochondrial activity in the treated tissue was validated in vivo by in-situ hybridization (see FIG. 4 in the main text). This shows additional evidence towards the activation of this independent pathway in this condition.

We then applied the proposed Maximum Impact Estimation (fully described in Materials and Methods) to the data set. The ranking obtained with the p-values corrected for crosstalk is shown in FIG. 14b and is greatly improved. The most significant pathway is the mitochondrial pathway, showing that greatly enhanced mitochondria activity continues to be the most important difference between the treated and untreated cells even after 7 days. This in turn suggests that the tissue underwent along-lasting remodeling phenomenon, in addition to a number of transitory phenomena such as cellular death and phagocytosis (note that the Phagosome pathway, significantly impacted after 3 days is not significant anymore after 7 days). The pathway ranked second is Arrhythmogenic Right Ventricular Cardiomiopathy. While this pathway was treated here as a false positive due to lack of literature evidence linking it specifically to tissue remodeling, the module reported by the method includes genes related to desmosomes, cell structures responsible for certain types of cellular adhesion which may also be relevant here. Fourth and fifth pathways in rank are, respectively, the PPAR Signaling pathway and the Cell Adhesion Molecules pathway, both closely related to the phenomenon of fat remodeling.

Estrogen treatment on post-menopausal women. The second data set we include here was produced by an experiment investigating the effect of various types of hormones on the endometrium of healthy, post-menopausal women who underwent hysterectomy. Hormone therapy has been used for the treatment of conditions associated with menopause. Estrogen replacement therapy has been proven useful against the insurgence of collateral effects of the post-menopausal syndrome. However, the administration of estrogens only has been shown to increase the incidence of endometrial carcinoma. Therefore, in addition to estrogen, progestins are now given to menopausal women. Although the risk of endometrial cancer is reduced with the addition of progestins, the incidence of other forms of cancer seems to increase when progestin is administered with estrogen. Initiatives like the Million Women Study and the Women Health Initiative showed that hormone replacement therapy can increase the risk of lung and breast cancer. In this context, it is interesting to compare the effects of various combinations of hormones at the transcriptome level.

Here, we illustrate our analysis method on the comparison of the expression levels of genes from samples treated with estrogen (E2) plus medroxyprogesterone acetate (MPA) versus normal samples. The classical over-representation analysis (ORA) finds the following pathways significant at the 5% level after FDR correction: ECM receptor interaction, Focal Adhesion, Pathways in Cancer, Small Cell Lung Cancer, Axon Guidance, Prostate Cancer, and Jak-STAT Signaling. These results are shown in FIG. 15a.

The E2+MPA is known to be associated with certain type of cancer including non-small-cell lung cancer (NSCLC). Hence, the presence of Pathways in Cancer is justified, even though its identification as significant does not help understand the specific mechanism that might be active here. However, the set of significant pathways include small-cell lung cancer (SCLC) which is not known to be associated with this treatment and fail to include the NSCLC which has been linked to it. Prostate Cancer is also unlikely to be related to this specific treatment given that this treatment is administered to women, rather than men. Like in the previous case, the presence of false positives and the presence of pathways describing general cellular adhesion processes (focal adhesion and ECM-receptor interaction) does not help with the understanding of the underlying phenomenon.

After applying our analysis method to the dataset, the results are more helpful in providing insights about the specific underlying mechanisms, as shown in FIG. 15b. The first pathway in the ranked list is the Jak-STAT signaling pathways. Indeed, there is evidence that estrogen treatments impact such pathway through interaction with the suppressor of cytokine signaling (SOCS). The second pathway is a new pathway, based on the module common between Focal Adhesion, ECM-receptor Interaction, and Pathways in Cancer (see the left panel of FIG. 16). In this figure, within the significant quadrant, the symmetric pattern that can be observed between the three pathways above and Pathways in Cancer indicate the presence of a functional module that responds specifically to the hormone treatment. Interestingly, this pathway is the same pathway that has been shown to be active in a completely different phenotype, the cervical ripening experiment described in the main text, the Integrin-Mediated ECM Signaling described in FIG. 6. This pathway is responsible for the significance of the top four pathways in FIG. 15a.

As in the experiment studying cervical ripening, this novel pathway is composed of genes present in the interaction between the cellular transmembrane protein integrin and three important ECM components, collagen, laminin, and fibronectin, all of which appeared as differentially expressed in hormone treatment compared to the control. This is interesting because the ECM-receptor interaction carries two major functions: the first is to transduce extracellular signals into the cell for regulation of downstream pathways possibly through focal adhesion complex, and the second function is to provide structural support to resident cells; the binding between integrins and collagen, laminin, fibronectin is involved in the second process. Collagen, a major component of the ECM, forms fibers and attaches to the cell surface through binding with integrins and fibronectins. Collagen is also present in the basement membrane with laminin, forming a thin sheet of fibers that underlies the epithelium. Previous studies have shown that collagen, laminin, and fibronectin participate in regulating normal development of mammalian mammary tissues. They also play an important role in cancer progression possibly through ECM remodeling, which leads to alterations in cell adhesion and tumor cell motility. Consistent with this, enhanced attachment of estrogen-dependent breast cancer cells to the substrate containing ECM components (collagen I and IV, laminin, fibronectin) was observed with E2 treatment. More evidence was provided in recent studies using mouse mammary epithelial cells, where the expression of estrogen receptor α (ERα) was greatly down-regulated by integrin-mediated interaction with collagen-IV and laminin, rather than effects of growth factors such as insulin. Consistently to the previous findings, our method finds that it is the module describing the interaction between integrin and collagen, laminin, and fibronectin (rather than the interaction between ligands and their receptors) that is affected specifically by the hormone treatment, a striking pattern unlikely to be detected by classical over-representation analysis.

A similar pattern was observed between pathways Prostate Cancer and Focal Adhesion, where the removal of a common submodule caused loss of significance in both pathways. A close investigation of the Focal Adhesion pathway revealed that its downstream signaling cascade is regulated by two types of extracellular signals, the ECM components that interact with integrins, and the growth factors (GFs) that bind to the transmembrane GF receptor (GFR). Although a number of DE genes belong to the ECM-Receptor Interaction pathway, it is the GFR-induced signaling cascade that is involved in both Prostate cancer and Focal adhesion, which contains at least two downstream pathways that responded specifically to the E2+MPA treatment. The first one is the canonical Wnt cascade, during which the transcription factor β-catenin gets activated by PI3K-AKT (phosphatidylinositol 3 kinase-V-Akt murine thymoma viral oncogene homolog) mediated signals, and translocate into the nucleus for downstream gene regulation. The other is the classical MAPK (Mitogen-Activated Protein Kinase) pathway, also known as the Raf-MEK-ERK pathway, where Raf (MAPKKK), MEK (MAPKK), and ERK (MAPK) represent the three key serine/threonine-specific protein kinases present in the cascade. What is also noticeable is that in both cases, while Wnt Signaling pathway and MAPK Signaling pathway both contain sub-pathways other than the two highlighted here, such as the Wnt5-induced non-canonical Wnt pathway or JNK-p38-mediated MAPK pathway, only the canonical Wnt cascade and the classical MAPK cascade are associated with both Prostate Cancer and Focal Adhesion, among which a number of important genes are DE under the hormone condition, such as PTEN (phosphatase and tensin homolog), a tumor suppressor that regulates PI3K-AKT signaling pathway, ERK (extracellular-signal-regulated kinase), one of the three key protein kinases in the MAPK pathway, and AR (androgen receptor), an oncogene that plays an important role in MAPK-regulated cell proliferation. Indeed, estradiol has been shown to activate β-catenin-mediated Wnt pathway through inhibition of its partner GSK3 in the rat hippocampus, which releases β-catenin and allows its nuclear translocation. More functional evidence was provided using human colon and breast cancer cells, in which estrogen receptor (ER) and β-catenin were found to participate in the same multi-protein complex, whose interaction gets enhanced with the presence of estrogen. Since both β-catenin and ER function as transcription factors, it is possible that the role of β-catenin in this complex is to recruit additional co-activators and chromatin remodeling factors that interact with ER for downstream transcriptional regulation. Estrogen has been demonstrated to induce cell proliferation through increased phosphorylation of MAPK cascade, with the mechanistic link between estrogen and MAPK signaling lying in a partner of ER, the MNAR (modulator of non-genomic activity of estrogen receptor) protein. MNAR forms a complex with ER and Src family of tyrosine kinases as a scaffold protein, which is enhanced by E2, further induces activation of ERK kinases and affects ER-mediated transcription. Consistent with these studies, our method detected a module shared between Prostate cancer and Focal adhesion, the GFR-induced canonical Wnt and classical MAPK cascade, which is responsible for significance of both pathways.

Another interesting case is shown in the right panel of FIG. 16. Here, the Graft-Versus-Host Disease pathway gains significance when the crosstalk of various other pathways is removed. This happens because all shared genes between Graft-Versus-Host Disease and the others are all non-DE genes in this condition. In other words, the DE genes present in Graft-Versus-Host Disease pathway are specific to the pathway itself. Among those, two particularly interesting ones are PRF1 (perforin 1) and GZMB (granzyme B), both of which play important functional roles in the natural killer (NK) cell-mediated cytolysis. Consistent with this, the Graft-Versus-Host Disease pathway is highlighted as being significantly affected by the E2+MPA treatment in the cross-talk matrix, not due to other interactions but due to genes specific to NK cell-mediated cytotoxicity. It is remarkable that the results of this type of analysis allowed the identification of a module, composed by genes belonging to the Graft-Versus-Host Disease pathway, that is impacted by the hormone treatment, and whose importance was masked by crosstalk effects with other pathways. This module is relevant in the condition studied, and treating it separately would provide a more accurate understanding of the underlying biological phenomenon. However, since the activity of this module was not identified yet in another condition, nor do we have an independent in vivo validation for this phenotype, we are not proposing this as an independent pathway at this time.

Crosstalk matrix for the cervical ripening experiment. The crosstalk matrix for the cervical ripening experiment indicates the presence of an independent functional module among the top three pathways in the ranking. The module is the same module found in the hormone treatment experiment, although in this experiment it is found from the interaction of different pathways. A detail of the crosstalk matrix is shown in FIG. 17.

Materials and Methods

The maximum impact estimation: an expectation maximization technique for the assessment of the significance of signaling pathways in presence of crosstalk. The crosstalk matrix is a useful tool for the interpretation of the effect of crosstalk between pathways. However, the ultimate goal of the analysis of signaling pathways is to provide a meaningful ranking among pathways, as well as a p-value quantifying the likelihood that a certain pathway is involved in the phenomenon in analysis. Here, we developed a correction method for the ranking of pathways that takes into account the overlaps between pathways.

The main idea is that if there is no crosstalk, then there is no ambiguity in the ORA significance calculations. In such a case, if genes in a pathway are over-represented, it cannot be a false positive caused by crosstalk. Our approach is therefore to infer an underlying pathway impact matrix where each gene contributes to one and only one pathway, hence is devoid of crosstalk, and then to perform the ORA using that impact matrix. Since this underlying pathway impact matrix is not observed directly, it is inferred through likelihood-based methods, and estimated using the EM algorithm. The corrected ranking is computed using ORA with the underlying pathway impact matrix, shown as follows.

Let us consider the DE indicator vector Y, representing the differential expression of genes, and the membership matrix X describing the membership of each gene in each one of k pathways $P_1 \ldots P_k$. The vector Y is defined as follows:

$$Y_i = \begin{cases} 1 & \text{if } g_i \text{ is } DE \\ 0 & \text{if } g_i \text{ is } NDE \end{cases}$$

and each cell $X_{i,j}$ of the matrix X is defined as follows:

$$X_{ij} = \begin{cases} 1 & \text{if } g_i \text{ belongs to } P_j \\ 0 & \text{if } g_i \text{ does not belong to } P_j \end{cases}$$

The matrix Y|X obtained by combining the vector Y with the X matrix is shown in the example in FIG. 18.

In many analysis methods, the membership matrix X is also interpreted as the impact matrix: if $X_{ij}$=1, then gene $g_i$ impacts pathway $P_j$. In ORA, for example, each gene is considered to have the same full impact on all pathways the gene belongs to. Crosstalk effects result from the fact that a gene can belong to more than one pathway, but in principle, it can potentially have a different biological impact on each such pathway. Our aim is to identify the pathway where the biological impact of such a shared gene is maximum. We do so by estimating the maximum impact pathway using an expectation maximization approach as described in the following.

Assuming that in a specific biological condition each gene distributes its impact differently to each pathway, we will consider the pathway to which each gene distributes the greatest fraction of its impact. We define a binary matrix Z that indicates, for each gene, the pathway that receives the biggest fraction of that gene's impact. For each gene $g_i$, the corresponding row $Z_i=[Z_{i1}, Z_{i2}, \ldots, Z_{ik}]$, where $Z_{ij} \in \{0,1\}$, will have $\Sigma_{j=1}^{k} Z_{ij}=1$, i.e., there is only one column in each row that has a non-zero element. This matrix Z is the unknown underlying pathway impact matrix referred to above; our goal is to estimate it.

Let us consider one row $Z_i$ having a one in an unknown column j and zeros elsewhere. Since we don't know j, we compute the probability of each pathway to be the one where gene $g_i$ gives the greatest fraction of its impact. To do this, we assume a non-negative vector of multinomial probabilities $\Pi=\{\pi_1 \ldots \pi_k\}$ with $\Sigma_{j=1}^{k}\pi_j=1$, defined by $\pi_j=p(Z_{ij}=1|Y_i=1)$. In other words, given a gene $g_i$ that is DE, $\pi_j$ is the probability that $g_i$ gives the greatest fraction of its impact to $P_j$. Similarly, we also define $\Theta=\{\theta_1 \ldots \theta_k\}$, where $\theta_j=p(Z_{ij}=1|Y_i=0)$ for the NDE genes.

Row i of the membership matrix X is denoted by $X_i$; this vector tells us which pathways gene i belongs to. Within the context of the probabilistic model described above, each row $X_i$ can be interpreted as an observation of a gene with a given expression state Y that give the greatest fraction of its impact to one of the pathways to one of the pathway it belongs to. Therefore, for DE genes we have $p(X_i=x_i|Y_i=1,\Pi)=\Pi \cdot x_i'$. We further assume that the hidden matrix Z is consistent with the observed X, i.e., $Z_{ij}$ can be 1 only when $X_{ij}=1$; if $X_{ij}=0$ then we must have $Z_{ij}=0$ (a gene cannot contribute most to a pathway that it does not belong to). With this notation:

$$p(Z_i = z_i | X_i = x_i, Y_i = 1, \Pi) = \frac{p(Z_i = z_i, X_i = x_i | Y_i = 1, \Pi)}{p(X_i = x_i | Y_i = 1, \Pi)} = \frac{I(z_i \cdot x_i' = 1) \cdot \Pi \cdot z_i'}{\Pi \cdot x_i'} \quad (1)$$

where I(.) is the indicator function. For example, if $x_i$=(11001) and $g_i$ is a DE gene, then the conditional distribution of $Z_i$ is given by:

$p(Z_i=(10000)|X_i=x_i,Y_i=1,\Pi)=\pi_1/(\pi_1+\pi_2+\pi_5)$ $p(Z_i=(01000)|X_i=x_i,Y_i=Y_i,1,\Pi)=\pi_2/(\pi_1+\pi_2+\pi_5)$ $p(Z_i=(00100)|X_i=x_i,Y_i=1,\Pi)=0$ $p(Z_i=(00010)|X_i=x_i,Y_i=1,\Pi)=0$ $p(Z_i=(00001)|X_i=x_i,Y_i=1,\Pi)=\pi_5/(\pi_1+\pi_2+\pi_5)$ (2)

This yields a vector of conditional probabilities $c_i=(c_{i1}, c_{i2}, \ldots, c_{ik})$ for each row $Z_i$ of DE genes, where $c_{ij}=p(Z_{ij}=z_{ij}|X_i=x_i)$ as defined above. Once those probabilities are estimated, we can produce a most likely matrix Z by assigning each gene to the pathway with the highest probability of receiving the biggest fraction of the impact of the gene. Specifically, $z_{ij}=1$ when $\max_s\{c_{is}\}=c_{ij}; z_{ij}=0$ otherwise.

If there were no crosstalk, each gene would contribute to a single pathway, the matrix X and the matrix Z would be equal, and they would have only one element equal to 1 in each row. In this case, $\pi_j$ could be estimated as the number of DE genes belonging to the pathway divided by the total number of DE genes. The probabilities $\pi$ and $\theta$ could be estimated as follows:

$$\hat{\pi}_j = \frac{\sum_{i=1}^{n} x_{ij}}{n} \quad (3)$$

$$\hat{\theta}_j = \frac{\sum_{i=n+1}^{n+m} x_{ij}}{m} \quad (4)$$

In the presence of crosstalk, however, it is not possible to compute $\Pi$ and $\Theta$ directly from X A likelihood-based estimation can be used instead.

The log-likelihood of observing the incidence matrix X given the gene expression vector Y is then:

$$\log L = \sum_{i=1}^{n+m} \log(p(X_i | Y_i; \pi_1, \pi_2, \pi_3, \ldots \pi_k, \theta_1, \theta_2, \theta_3 \ldots \theta_k)) \quad (5)$$

Equation 5 is written under the assumption of conditional independence of rows of X; i.e., under the reasonable assumption that the pathway to which a gene i gives most of its impact does not depend on the pathway to which another gene j impacts the most. In other words, the split of the fractions of the impact of a gene does not depend the splits of the impact of other genes.

This assumption, together with the observation that the DE genes do not depend on $\theta$'s and that the NDE genes do not depend on $\pi$'s, allows us to compute the likelihood by separating the matrix in two sub-matrices: X|Y=1, representing the sub-matrix of the DE genes, and X|Y=0, representing the sub-matrix of the NDE genes:

$$\log L = \sum_{i=1}^{n} \log(p(X_i | Y_i = 1, \Pi)) + \sum_{i=n+1}^{m+n} = \quad (6)$$

$$\log(p(X_i | Y_i = 0, \Theta)) = \sum_{i=1}^{n} \log(\Pi \cdot X_i') + \sum_{i=n+1}^{m+n} \log(\Theta \cdot X_i')$$

In the following, we will only work with the first term to illustrate how to estimate $\Pi$. $\Theta$ can be estimated from X|Y=0 in a similar fashion.

There is no closed form solution for the maximization of Eq. 6. However, we can use the Z matrix as a hidden variable for the estimation of the parameters Π. The log joint conditional likelihood for the DE part of the matrix can be written as:

$$\log JL^{DE} = \log(p(X, Z \mid Y = 1, \Pi)) = \sum_{i=1}^{n} \log(p(X_i, Z_i \mid Y_i = 1, \Pi)) = \quad (7)$$

$$\sum_{i=1}^{n} \log(I(Z_i^{DE} \cdot (X_i^{DE})' = 1) \cdot Z_i^{DE} \cdot \Pi) =$$

$$\sum_{i=1}^{n} \log\left( I(Z_i^{DE} \cdot (X_i^{DE})' - 1)) \cdot \sum_{j=1}^{k} Z_{ij}^{DE} \cdot \log(\pi_j) \right) =$$

$$\sum_{i=1}^{n} \log\left( \sum_{j=1}^{k} z_{ij}^{DE} \cdot x_{ij}^{DE} \right) + \sum_{i=1}^{n} \sum_{j=1}^{k} \log(\pi_i) \cdot z_{ij}^{DE}$$

We use an expectation maximization (EM) approach to maximize the log likelihood in Equation 5 by maximizing the joint log likelihood defined in Equation 7. The EM is an iterative algorithm that starts with an initial guess for Π, denoted with $\Pi^0$; each iteration is a mapping between $\Pi^t$ and $\Pi^{t+1}$. The superscript indicates the index of the iteration. We choose to initialize each element of the vector as follows:

$$\pi_j^0 = \frac{\sum_{i=1}^{n} x_{i,j}}{\sum_{i=1}^{n} \sum_{h=1}^{k} x_{i,h}}, \; j \in \{1 \ldots k\} \quad (8)$$

This initialization is consistent with the model described in Equation 3.

Each iteration of the EM algorithm is composed by two steps: the expectation step and the maximization step; during the expectation step we compute the expectation of the log joint conditional likelihood in Equation 7 with respect to the posterior $p(Z_{i,j}^{DE} \mid Z_i^{DE}, \Pi^{old})$:

$$E\left( \sum_{i=1}^{n} \log\left( \sum_{j=1}^{k} z_{i,j}^{DE} \cdot x_{i,j}^{DE} \right) + \sum_{i=1}^{n} \sum_{j=1}^{k} \log(\pi_j) \cdot z_{i,j}^{DE} \right) = \quad (9)$$

$$E\left( \sum_{i=1}^{n} \log\left( \sum_{j=1}^{k} z_{i,j}^{DE} \cdot x_{i,j}^{DE} \right) \right) + E\left( \sum_{i=1}^{n} \sum_{j=1}^{k} \log(\pi_j) \cdot z_{i,j}^{DE} \right) =$$

$$E\left( \sum_{i=1}^{n} \sum_{j=1}^{k} \log(\pi_j) \cdot z_{i,j}^{DE} \right)$$

The term $E\left( \sum_{i=1}^{n} \log(\sum_{j=1}^{k} z_{i,j}^{DE} \cdot x_{i,j}^{de}) \right)$ is equal to 0 because the term $\sum_{j=1}^{k} z_{i,j}^{DE} \cdot x_{i,j}^{DE}$ is equal to 1 for the consistency of Z with X.

The derivation of the non zero term of the expectation is as follows:

$$E\left( \sum_{i=1}^{n} \log\left( \sum_{j=1}^{k} z_{i,j}^{DE} \cdot x_{i,j}^{DE} \right) \right) \quad (10)$$

-continued $$\sum_{j=1}^{k} z_{i,j}^{DE} \cdot x_{i,j}^{DE}$$

$$E\left( \sum_{i=1}^{n} \sum_{j=1}^{k} \log(\pi_j) \cdot z_{i,j}^{DE} \right) = \sum_{i=1}^{n} \sum_{j=1}^{k} \log(\pi_j) \cdot E\left( z_{i,j}^{DE} \mid X_{i,j}^{DE}, \Pi^{old} \right) =$$

$$\sum_{i=1}^{n} \sum_{j=1}^{k} \log(\pi_j) \cdot p\left( z_{i,j}^{DE} = 1 \mid X_i^{DE}, \Pi^{old} \right) =$$

$$\sum_{i=1}^{n} \sum_{j=1}^{k} \log(\pi_j) \cdot \frac{p\left( z_{i,j}^{DE}, X_i^{DE} \mid \Pi^{old} \right)}{\sum_{r=1}^{k} p\left( z_{i,j}^{DE}, X_i^{DE} \mid \Pi^{old} \right)} =$$

$$\sum_{i=1}^{n} \sum_{j=1}^{k} \log(\pi_j) \cdot \frac{x_{i,j}^{DE} \cdot \pi_j^{old}}{\sum_{r=1}^{k} x_{i,j}^{DE} \cdot \pi_r^{old}}$$

The maximization of the expectation with respect to Π, subject to the constraint that $\sum_{j=1}^{k} \pi_j = 1$, is obtained with the Lagrange multiplier method as follows:

$$\sum_{j=1}^{k} \pi_j = 1 \quad (11)$$

$$\frac{d\left[ \sum_{j=1}^{k} \log(\pi_j) \sum_{i=1}^{n} \frac{x_{i,h} \cdot \pi_h^{old}}{\sum_{r=1}^{k} x_{i,r} \cdot \pi_r^{old}} + \lambda\left(\left(\sum_{j=1}^{k} \pi_j\right) - 1\right) \right]}{d\pi_h} = 0,$$

$$\forall h \in \{1 \ldots k\}$$

$$\frac{\sum_{i=1}^{n} \frac{x_{i,h} \cdot \pi_h^{old}}{\sum_{r=1}^{k} x_{i,r} \cdot \pi_r^{old}}}{\pi_h} + \lambda = 0, \; \forall h \in \{1 \ldots k\}$$

We can write a systems of equations over all the possible values of h in order to compute λ.

$$\begin{cases} \sum_{i=1}^{n} \frac{\frac{x_{i,1} \cdot \pi_1^{old}}{\sum_{r=1}^{k} x_{i,r} \cdot \pi_r^{old}}}{\pi_1} + \lambda = 0 \\ \vdots \\ \sum_{i=1}^{n} \frac{\frac{x_{i,k} \cdot \pi_k^{old}}{\sum_{r=1}^{k} x_{i,r} \cdot \pi_r^{old}}}{\pi_k} + \lambda = 0 \end{cases}$$

-continued $$\begin{cases} \sum_{i=1}^{n} \frac{x_{i,1} \cdot \pi_1^{old}}{\sum_{r=1}^{k} x_{i,r} \cdot \pi_r^{old}} = -\lambda \cdot \pi_1 \\ \vdots \\ \sum_{i=1}^{n} \frac{x_{i,k} \cdot \pi_k^{old}}{\sum_{r=1}^{k} x_{i,r} \cdot \pi_r^{old}} = -\lambda \cdot \pi_k \end{cases}$$

Summing left and right sides we obtain:

$$\sum_{j=1}^{k} \sum_{i=1}^{n} \frac{x_{i,j} \cdot \pi_j^{old}}{\sum_{r=1}^{k} x_{i,r} \cdot \pi_r^{old}} = -\lambda \sum_{j=1}^{k} \pi_j \quad (12)$$

Since $\sum_{j=1}^{k} \pi_j = 1$, we can write:

$$\lambda = -\sum_{j=1}^{k} \sum_{i=1}^{n} \frac{x_{i,j} \cdot \pi_j^{old}}{\sum_{r=1}^{k} x_{i,r} \cdot \pi_r^{old}} \quad (13)$$

We substitute $\lambda$ in 11 and use an iterative process in which a new $\pi$ value is calculated at each step:

$$\frac{\sum_{i=1}^{n} \frac{x_{i,j} \cdot \pi_j^{old}}{\sum_{r=1}^{k} x_{i,r} \cdot \pi_r^{old}}}{\pi_h^{new}} + \lambda = 0, \forall h \in \{1 \ldots k\} \quad (14)$$

$$\frac{\sum_{i=1}^{n} \frac{x_{i,j} \cdot \pi_j^{old}}{\sum_{r=1}^{k} x_{i,r} \cdot \pi_r^{old}}}{\pi_h^{new}} - \sum_{j=1}^{k} \sum_{i=1}^{n} \frac{x_{i,j} \cdot \pi_j^{old}}{\sum_{r=1}^{k} x_{i,r} \cdot \pi_r^{old}} = 0,$$

$$\forall h \in \{1 \ldots k\}$$

$$\frac{\sum_{i=1}^{n} \frac{x_{i,h} \cdot \pi_h^{old}}{\sum_{r=1}^{k} x_{i,r} \cdot \pi_r^{old}}}{\pi_h^{new}} = \sum_{j=1}^{k} \sum_{i=1}^{n} \frac{x_{i,j} \cdot \pi_j^{old}}{\sum_{r=1}^{k} x_{i,r} \cdot \pi_r^{old}} = 0, \forall h \in \{1 \ldots k\}$$

$$\pi_h^{new} = \frac{\sum_{i=1}^{n} \frac{x_{i,h} \cdot \pi_h^{old}}{\sum_{r=1}^{k} x_{i,r} \cdot \pi_r^{old}}}{\sum_{j=1}^{k} \sum_{i=1}^{n} \frac{x_{i,j} \cdot \pi_j^{old}}{\sum_{r=1}^{k} x_{i,r} \cdot \pi_r^{old}}}, \forall h \in \{1 \ldots k\}$$

The algorithm stops when the distance between two consecutive vectors $\|\Pi^{(t)} - \Pi^{(t-1)}\|$ is less than the quantity $$\frac{\|\pi^1 - \pi^0\|}{100},$$

i.e. the distance between the first two vectors divided by 100. At the end of the steps of the EM algorithm we obtain the matrix C from which we can obtain the most probable Z given the condition under study: for each row, we assign the value 1 to the cell with the highest probability, and 0 to all the others. This is equivalent to saying that each gene gives its full impact to the pathway with the highest $\pi$ value.

Choice for the threshold for the module detection procedure. The value 0.25 for the module selection procedure was selected by calculating all modules for all data sets with different thresholds in the [0, 0.4] range (with a difference of 0.025 between thresholds). The results are shown in FIG. 19. As it can be seen in the figure, the number of modules found in all data sets shows a plateau in the [0.1, 0.375] range.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

As illustrated in FIG. 20, the apparatuses and methods described above a preferably implemented by a programmed computer having at least one processor 100 coupled to a memory circuit, or circuits 102 (comprising a non-transitory computer-readable medium) encoded with executable programs, such as executable program 104 described below. The processor(s) 100 access the memory circuit(s) 102 to perform the algorithms described above and also described in the executable programs below. In addition to storing the executable programs, the memory circuit(s) also store in suitably configured data structures 106 the matrices, tables and intermediate computational values described above and also described in the executable programs. It will be understood that these matrices, tables and intermediate computational values are stored using data structures defined in the memory circuit(s) so as to hold the digital data upon which the described algorithms operate.

Although any of a number of programming languages and programming platforms may be used, one presently preferred implementation is written in the R programming language. In the implementation described, the concepts of the disclosed technology have been applied to a use case where the nodes are genes, where the measured difference attribute designates that the gene is (or is not) differentially expressed. Of course, the disclosed program code can be readily adapted to address other use cases, such as where the nodes are transcripts, gene products, RNA, proteins, biochemical compounds, and the like.

Description of Program Code (Algorithms) by which Processor(s) are Programmed

FIG. 20 illustrates the basic steps to detect the presence of crosstalk. Beginning at step 120, the processor(s) populate the pathway data structure and node data structure with data corresponding to at least a first pathway Pi and a second pathway Pj.

Next at step 122, the processor(s) manipulate the data stored in the pathway and node data structures to compute a p-value and store the computed p-values as first p-value data in the p-value data structure.

Then at step 124, the processor(s) manipulate the data stored in the pathway and node data structures to identify and remove from the pathway data structure intersecting nodes that are common to both first and second pathways to thereby define a modified data set.

Next at step 126, the processor(s) manipulate the modified data set to compute a p-value and store the computed p-values as second p-value data in the p-value data structure, and at step 128, compare the stored first and second p-value data and based on the comparison makes a determination whether crosstalk is present between the first and second pathways according to whether the first and second p-values differ from one another.

Finally, at step 120 the processor(s) provide an indication to a user of the apparatus of whether crosstalk is present between the first and second pathways.

The R-language program code to implement the algorithmic steps shown in FIG. 16 is more fully described by the following program code:

```
shortTitle <- function(x){
  if(nchar(x) < 23){
    shortTitle <- x
  }else{
    shortTitle <- paste(substr(x,1,10), substr(x, nchar(x)-9, nchar(x)), sep = "...")
  }
  shortTitle
}
crossTalk <- function(reference, selection, organism="hsa", path.info = NULL, shortTitles=TRUE){
  #computes the crossTalk between pathways, given a pathway set and a list of DE genes
  #
  # Args:
  #  reference: the reference file from which the list of DE genes has been extracted
  # selection: the list of DE genes
  # pathway.data: the pathway set in a specific format TODO ADD FORMAT; if NULL, the pathways from the SPIA package are used
  # Returns:
  #  hypermatrix: a matrix that has on the diagonal all the hypergeometric p-values of all the pathways, and in position i,j the hypergeometric p-value of the "crescent moon" obtained removing all the elements of pathway j from pathway i.
  # overlap.data: a bidimensional list with the intersections between all the pairs of pathways
  # TODO: change these locations to absolute and maybe produce a package for crossTalk computations
  source ("~/Workspaces/xtalk/r_utils/hypermatrix.crescentmoon.R")
  source ("~/Workspaces/xtalk/r_utils/overlapLists.R")
  source ("~/Workspaces/xtalk/r_utils/crescentMoonGenes.R")
  if(is.null(path.info)){
    ## if pathway data is NULL we use spia, otherwise the pathway data must be provided
    ## loading pathway data from SPIA
    library(SPIA)
    load(file = paste(system.file("extdata", package = "SPIA"), paste("/", organism, "SPIA", sep = ""), ".RData", sep = ""))
    pathway.data <- list( )
    pathGenes <- c( )
    path.titles <- NULL
    for (jj in 1:length(names(path.info))){
        ob <- path.info[[jj]]
        pathway.data[[jj]] <- ob$nodes
        pathGenes <- c(pathGenes,ob$nodes)
        path.titles <- c(path.titles, ob$title)
    }
    ## pathGenes is only for testing (and it proved to be useful)
    pathGenes <- unique(pathGenes)
    ## total genes is the number of genes in the reference
    ref <- as.character(ref)
    total.genes <- length(ref)
    names(pathway.data) <- names(path.info)
    how.many.pws <- length(path.info)
  }else{
    pathway.data <- list( )
    pathGenes <- c( )
    path.titles <- NULL
    for (jj in 1:length(names(path.info))){
        ob <- path.info[[jj]]
        pathway.data[[jj]] <- ob$nodes
        pathGenes <- c(pathGenes,ob$nodes)
        path.titles <- c(path.titles, ob$title)
    }
    ## pathGenes is only for testing (and it proved to be useful)
```

```
      pathGenes <- unique(pathGenes)
      ## total genes is the number of genes in the reference
      ref <- as.character(ref)
      total.genes <- length(ref)
      names(pathway.data) <- names(path.info)
      how.many.pws <- length(path.info)
    }
    ## data is loaded, now compute the hypermatrix
    ## TODO: change hypermatrix so that it has fisher test instead of phyper
    hyper.matrix      <-      hypermatrix.crescentmoon(pathway.list=pathway.data,
geneSel=selection, total.genes=ref)
      if(shortTitles){
        dimensionNames <- sapply(path.titles, shortTitle)
      }else{
        dimensionNames <- path.titles
      }
      rownames(hyper.matrix) <- colnames(hyper.matrix) <- dimensionNames
      ##      rownames(hyper.matrix)      <-      colnames(hyper.matrix)      <-
substr(path.titles,1,12)
      ## mat <- hyper.matrix
      temp.hyper <- hyper.matrix
      pvalues <- diag(hyper.matrix)[order(diag(hyper.matrix))]
      adjusted.pvalues <- p.adjust(pvalues, 'fdr')
      ## temp.hyper[temp.hyper==0] <- min(temp.hyper[temp.hyper!=0])
      mat <- -log10(temp.hyper)
      mat[ mat==Inf ] <- 0
      order.pvalues <- order(diag(mat), decreasing=TRUE)
      mat <- mat[order.pvalues,]
      mat <- mat[,order.pvalues]
      thr.index1p <- max( which(adjusted.pvalues < 0.01))
      thr.index5p <- max( which(adjusted.pvalues < 0.05))
      thrsh1p <- c(thr.index1p,dim(mat)[1]-thr.index1p)+0.5
      thrsh5p <- c(thr.index5p,dim(mat)[1]-thr.index5p)+0.5
      heatMapRes <- list(map=mat, thr1p=thrsh1p, thr5p=thrsh5p)
      ## overlap data
      overlapData <- overlaps(pathway.data, selection)
      overlapData$degenes       <-      overlapData$degenes[order.pvalues,
order.pvalues]
      overlapData$overlap <- overlapData$overlap[order.pvalues, order.pvalues]
      ## pathways info
      pathwaysInfo <- list( )
      pathwaysInfo$pathData <- pathway.data[order.pvalues]
      pathwaysInfo$pathTitles <- path.titles[order.pvalues]
      ## crescent moon info
      crescentMoonData <- crescentMoonGenes(pathway.data, selection)
      crescentMoonData$crescentMoon                                       <-
crescentMoonData$crescentMoon[order.pvalues, order.pvalues]
      crescentMoonData$deCrescentMoon                                     <-
crescentMoonData$deCrescentMoon[order.pvalues, order.pvalues]
      ## result
      crosstalk      <-      list(heatmap=heatMapRes,   overlapData=overlapData,
pathwaysInfo=pathwaysInfo, crescentMoonData = crescentMoonData)
    }
```

Computation of Independent Functional Modules

In a presently preferred embodiment, the program code by which the processor(s) identify potential independent functional modules is set forth in the following R-code:

```
    in Ref <- function(x,reference){
        in Ref <- sum(x %in% reference)
        in Ref
    }
    fisherset <- function(set,ref,sel){
        path <- set[set %in% ref]
        cmvect <- c(
            sum(path %in% sel),
            sum(!path %in% sel),
            length(sel)-sum(path %in% sel) ,
            length(ref[!(ref %in% path) & !(ref %in% sel)])
            )
        cmatrix <- matrix(cmvect,nrow=2)
        fres <- fisher.test(cmatrix, alternative='g')
        fisherset <- fres$p.value
        fisherset
    }
```

```
    jaccardd <- function(x,y){
        jaccardd <- 1 - length(intersect(x,y))/min(length(x),length(y))
        jaccardd
    }
    collapseNames <- function(modName, pNamesIds){
        pnames <- pNamesIds[unlist(strsplit(modName," "))]
        pnames <- gsub(" ","",pnames)
        pnames <- substr(pnames,1,8)
        pnames <- paste(pnames,collapse="+")
    }
    addModules <- function(pathwayData, ref, sel, pathwayTitles, thresholds,
distanceThreshold, verbose=TRUE){
        # thresholds are the thresholds we want to test in the form of a vector with
the numeric thresholds.
    ## e.g.: c(0.01, 0.05)
    # distanceThreshold is the threshold under which modules are merged
    pvals <- sapply(pathwayData, fisherset, ref=ref, sel=sel)
    orderp <- order(pvals)
    pvals <- pvals[orderp]
    pvals <- p.adjust(pvals,'fdr')
    #thrs <- c(max(which(pvals<0.01)), max(which(pvals< 0.05)))
    thrs <- NULL
    for(i in 1:length(thresholds)){
        thrs <- c(thrs, max(which(pvals < thresholds[i])))
    }
    names(thrs) <- thresholds
    thrs <- thrs[!duplicated(thrs)]
    thrs <- thrs[!is.infinite(thrs)]
    if(length(thrs)==0){
        moduleList = NULL
        cat("There is no significant pathway for any of the specified
thresholds. No modules will be found at this stage.")
        return(list(pathways=pathwayData, titles=c(pathwayTitles)))
    }
    pNamesIds <- pathwayTitles[orderp]
    pathwayDataOrdered <- pathwayData[orderp]
    names(pNamesIds) <- names(pathwayDataOrdered)
    if(verbose) cat("pNameIds generated, searching for modules\n")
    moduleList <- list( )
    for(t in 1:length(thrs)){
        threshold <- as.numeric(names(thrs)[t])
        if(verbose) cat("searching threshold", t, ":", names(thrs)[t], '\n')
        if(t == 1){
            start = 1
        }else{
            start <- thrs[t-1]
        }
        for(i in start:thrs[t]){
            for(j in start:thrs[t]){
                if(i < j){
                    # creation of the three pathways
                    bait <- pathwayDataOrdered[[i]]
                    prey <- pathwayDataOrdered[[j]]
                    #those are the new pathways to be created
                    baitcm <- bait[!bait %in% prey]
                    preycm <- prey[!prey %in% bait]
                    overlap <- bait[bait %in% prey]
                    pDataTemp <- pathwayDataOrdered
                    pDataTemp[[i]] <- baitcm
                    namei    <-   paste(names(pDataTemp)[i],    'minus',
names(pDataTemp)[j])
                    namej    <-   paste(names(pDataTemp)[j],    'minus',
names(pDataTemp)[i])
                    nameo    <-   paste(names(pDataTemp)[i],   'overlap',
names(pDataTemp)[j])
                    names(pDataTemp)[i] <- namei
                    pDataTemp[[j]] <- preycm
                    names(pDataTemp)[j] <- namej
                    pDataTemp[[length(pDataTemp)+1]] <- overlap
                    names(pDataTemp)[length(pDataTemp)] <- nameo
                    # now the list is modified, I compute the pvalues
                    pvalues    <-    sapply(pDataTemp,fisherset,ref=ref,
sel=sel)
                    # correct pathways and determine if i is not significant
anymore, j is not significant anymore, and overlap is significant (I will use
threshold 1 now, but I can use both)
```

```
                    padj <- p.adjust(pvalues, 'fdr')
                    if( (padj[length(padj)] <= threshold) & (padj[i] >
threshold) & (padj[j] > threshold) ){
                        ## the overlap is significant, the crescent
moons are not
                        ## now I need to check if there is another
pathway other than i and j in which the overlap is
                        moduleList[[length(moduleList)+1]] <- overlap
                        names(moduleList)[length(moduleList)]        <-
nameo
                    }
                }
            ## if(verbose) cat(i,j,'\n')
            if(verbose) cat('*')
            }
        }
        if(verbose) cat('\n')
    }
    if(length(moduleList)==0){
        moduleList <- NULL
        cat("No modules found!")
        return(list(pathways=pathwayData, titles=pathwayTitles))
    }
    if(verbose) cat("computing jaccard matrix\n")
        jaccardMatrix            <-           matrix(1,nrow=length(moduleList),
ncol=length(moduleList))
    for(i in 1:length(moduleList)){
        for(j in 1:length(moduleList)){
            jaccardMatrix[i,j] <- jaccardd(moduleList[[i]], moduleList[[j]])
        }
    }
    if(verbose) cat("merging modules\n")
    jaccardMatrixTmp <- jaccard Matrix
    moduleListTmp <- moduleList
    endIt <- FALSE
    count <- 1
    while(!endIt){
    skip=FALSE
        ## if(verbose) cat(count,'\n')
        endIt <- TRUE
        for(i in 1:length(moduleListTmp)){
            for(j in 1:length(moduleListTmp)){
                if(verbose) cat('*')
                if(j > i){
                    if( (jaccardMatrixTmp[i,j] < distanceThreshold)
& ( jaccardMatrixTmp[i,j] == min(jaccardMatrixTmp[upper.tri(jaccardMatrixTmp)])
) ){
                        # this means that there is a change in
the matrix: two modules will merge
                            moduleName                             <-
paste(names(moduleListTmp)[i], names(moduleListTmp)[j])
                            newModule                              <-
union(unlist(moduleListTmp[[i]]), unlist(moduleListTmp[[j]]))
                            moduleListTmp <- moduleListTmp[-c(i,j)]
    moduleListTmp[[length(moduleListTmp)+1]] <- newModule
    names(moduleListTmp)[length(moduleListTmp)] <- moduleName
                            # we will skip the remaining modules,
we will see in the next
                            skip <- TRUE
                            endIt <- FALSE
                            break
                    }
                }
            }
            if(skip){
                    jaccardMatrixTmp                               <-
matrix(1,nrow=length(moduleListTmp), ncol=length(moduleListTmp))
                for(i in 1:length(moduleListTmp)){
                    for(j in 1:length(moduleListTmp)){
                        jaccardMatrixTmp[i,j]                      <-
jaccardd(moduleListTmp[[i]], moduleListTmp[[j]])
                    }
                }
                skip = FALSE
                break
            }
        }
        cat(count,'\n')
        count <- count+1
```

```
        }
        if(verbose) cat ('\n')
        if(verbose) cat("cleaning names\n")
        namesList <- lapply(names(moduleListTmp),function(x) strsplit(gsub("
overlap "," ",x)," "))
        removals <- lapply(namesList, function(x) sort(unique(unlist(x))))
        namesList <- sapply(namesList,function(x) paste(sort(unique(unlist(x))),
collapse=''))
        names(moduleListTmp) <- namesList
        #Remove module i from pathways with ID in removals[i]
        modulesTitles <- unlist(lapply(names(moduleListTmp), collapseNames,
pNamesIds=pNamesIds))
        if(verbose) cat("removing modules from parent pathways\n")
        pathwayDataMod <- pathwayDataOrdered
        for(i in 1:length(pathwayDataMod)){
            for(j in 1:length(moduleListTmp)){
                if(names(pathwayDataMod)[i] %in% removals[[j]]){
                    pathwayDataMod[[i]]                                    <-
<-setdiff(pathwayDataMod[[i]],moduleListTmp[[j]])
                    pNamesIds[names(pathwayDataMod)[i]] <- paste("*",
pNamesIds[names(pathwayDataMod)[i]])
                }
            }
        }
        pathwayDataMod <- c(pathwayDataMod, moduleListTmp)
        ## names(pathwayDataMod) <- c(pNamesIds, modulesTitles)
        names(modulesTitles) <- names(moduleListTmp)
        addModules <- list(pathways=pathwayDataMod, titles=c(pNamesIds,
modulesTitles))
    }
```

Computation of p-Values

In a presently preferred embodiment, the program code by [30] which the processor(s) compute and manipulate quantitative p-values is set forth in the following R-code:

```
    hypermatrix.crescentmoon <- function(pathway.list, geneSel, total.genes,
lower.tail=FALSE){
        n.pathways <- length(pathway.list)
        res.matrix <- matrix(1, nrow=n.pathways, ncol=n.pathways)
        ntot <- length(total.genes)
        for(i in 1:n.pathways){
          bait.genes <- pathway.list[[i]]
          nde.bait <- sum(bait.genes %in% geneSel)
          ntot.bait <- sum(bait.genes %in% total.genes)
          for(j in 1:n.pathways){
            prey.genes <- pathway.list[[j]]
            nde.prey <- sum(prey.genes %in% geneSel)
            ntot.prey <- sum(prey.genes %in% total.genes)
            overlap.genes <- bait.genes[bait.genes %in% prey.genes]
            nde.overlap <- sum(overlap.genes %in% geneSel)
            ntot.overlap <- sum(overlap.genes %in% total.genes)
            if(j!=i)
              res.matrix[i,j] <- phyper(nde.bait-nde.overlap-1, ntot.bait-ntot.overlap,
ntot-ntot.bait+ntot.overlap, length(geneSel), lower.tail=lower.tail)
            if(i==j)
              res.matrix[i,j]   <-   phyper(nde.bait-1,   ntot.bait,   ntot-ntot.bait,
length(geneSel), lower.tail=lower.tail)
          }
        }
        rownames(res.matrix) <- colnames(res.matrix) <- names(pathway.list)
        hypermatrix.crescentmoon <- res.matrix
    }
```

Additional program code by which to implement the described apparatuses and methods may be found in the Appendix.

Appendix

```
crescentMoonGenes <- function(pathwayList, selection){ nPathways <- length(pathwayList)
  pathwayNames <- names(pathwayList)
  resList <- list()
  crescentMoon <- list()
  deCrescentMoon <- list()
  for(i in 1:nPathways){
    baitGenes <- pathwayList[[i]]
nde.bait <- sum(baitGenes %in% geneSel)
    for(j in 1:nPathways){
      preyGenes <- pathwayList[[j]]
nde.prey <- sum(preyGenes %in% geneSel)
      crescentMoonGenes <- baitGenes[!(baitGenes %in% preyGenes)]
```

```
nde.overlap <- sum(overlapGenes %in% geneSel)
      crescentMoon[[(i-1)*nPathways+j]] <- crescentMoonGenes
      deCrescentMoon[[(i-1)*nPathways+j]]                        <-
crescentMoonGenes[crescentMoonGenes %in% selection]
    }
  }
  cmGenes <- matrix(crescentMoon, nrow=nPathways, byrow=TRUE)
  cmDegs <- matrix(deCrescentMoon, nrow=nPathways, byrow=TRUE)
  rownames(cmGenes) <- rownames(cmDegs) <- colnames(cmGenes) <-
colnames(cmDegs) <- pathwayNames
  resList$crescentMoon <- cmGenes
  resList$deCrescentMoon <- cmDegs
  resList

}
================== rm(list=ls())

setwd("~/Workspaces/xtalk/mice_data/")

# prepare stuff once and for all
source("~/Workspaces/xtalk/r_utils/emutils.R")
source("~/Workspaces/xtalk/r_utils/moduleList.R")
source("~/Workspaces/xtalk/r_utils/imagePlotMod.R")
source("~/Workspaces/r_utils/crossTalk.R")
source("~/Workspaces/xtalk/r_utils/linksMatrix.R")
source("~/Workspaces/xtalk/r_utils/mieUtils.R")

EXPERIMENTID
expid <- 'mice-data'

Change organism
organism <- 'mmu' load(file = paste(system.file(package="SPIA"), paste("/extdata/", organism,
"SPIA", sep = ""), ".RData", sep = ""))
  load("mmuSPIA1.8.0.RData")
  pathway.data <- list()
```

```
pathGenes <- c()
path.titles <- NULL
for (jj in 1:length(names(path.info))){
  ob <- path.info[[jj]]
  pathway.data[[jj]] <- ob$nodes
  pathGenes <- c(pathGenes,ob$nodes)
  path.titles <- c(path.titles, ob$title)
}
pathGenes <- unique(pathGenes)
names(pathway.data) <- names(path.info)

setwd("~/Workspaces/xtalk/mice_data/")
```

THE DATA HAS TO BE PROVIDED IN A VECTOR (NAMED dedata) WITH THE INFORMATION ABOUT THE GENE BEING DIFFERENTIALLY EXPRESSED OR NOT, THE NAMES BEING ENTREZ GENE IDS

```
#preparation of the data
dataTable <- read.table("day3_all.txt", stringsAsFactors=F, header=T)
dataTable <- dataTable[!duplicated(dataTable$Accession),]
rownames(dataTable) <- dataTable[,1]
dataTable <- dataTable[,c(2,3,7)]
colnames(dataTable) <- c("day0","day3", "pvalue")

Reference extraction:
ref3.acc <- rownames(dataTable)
map2entrez.df <- read.table("map2entrez.csv",   stringsAsFactors = F, sep=";")
  acc2entrez <- map2entrez.df$V2
  names(acc2entrez) <- map2entrez.df$V1
  ref3.entrez <- acc2entrez[ref3.acc]
  ref3.entrez <- ref3.entrez[!is.na(ref3.entrez)]
  ref3.entrez <- unique(ref3.entrez)

dedata <- rep(FALSE, length(ref3.entrez))
  names(dedata) <- ref3.entrez dataTable <- dataTable[order(dataTable$pvalue, decreasing=FALSE),]

dataTable.sel <- dataTable[1:floor(dim(dataTable)[1]*0.05),]
```

```
dataTable.sel <- rownames(dataTable.sel)
dataTable.sel.en <- acc2entrez[dataTable.sel]
dataTable.sel.en <- dataTable.sel.en[!is.na(dataTable.sel.en)]
dataTable.sel.en <- unique(dataTable.sel.en)

dedata[names(dedata) %in% dataTable.sel.en]=TRUE ref <- names(dedata)
sel <- names(dedata)[dedata==1]

modList <- addModules(pathway.data, ref, sel, path.titles, c(0.01,0.05), 0.25)

pathway.dataMod <- modList$pathways
  names(pathway.dataMod) <- modList$titles creation of emmatrix for alin
how.many.pws <- length(pathway.dataMod)
emmatrix <- matrix(0,nrow=length(dedata), ncol=how.many.pws+1)
rownames(emmatrix) <- names(dedata)
colnames(emmatrix) <- c("DE", names(pathway.dataMod))
emmatrix <- as.data.frame(emmatrix)
emmatrix[,1] = as.numeric(dedata)
for(i in 2:(how.many.pws+1)){
  emmatrix[,i] <- as.numeric(names(dedata) %in% pathway.dataMod[[i-1]])
} write.csv(emmatrix, file="mice_3vs0_pathways_modules.csv")
```

\# test: since non significant pathways give inconsistent results, I will compute the MIEMatrices
  \# only for pathways under the .10 threshold (can be changed later)

\#\# compute the hypergeometric p-values of original pathways

\# pass only the pathways for which the phyp is less than 0.1

```
    MIEMatrices <- mieMatrices(deData = dedata, pathwayData =
pathway.dataMod, xThreshold=.1, stopThreshold=1e-2, verbose=T)
    emmatrixDE <- MIEMatrices$EMMatrixDE
    emmatrixNDE <- MIEMatrices$EMMatrixNDE totalGenes <- length(ref)
    totalDE <- length(sel)
    ## this chooses only the max probability and sets it at 1
    emmatrixDEMod <- t(apply(emmatrixDE, 1, zeroRow))
    emmatrixNDEMod <- t(apply(emmatrixNDE, 1, zeroRow))

deVect <- apply(emmatrixDEMod, 2, sum)
    ndeVect <- apply(emmatrixNDEMod, 2, sum)

names(deVect) <- names(ndeVect) <- names(pathway.dataMod)

correctedRanking <- mapply(doFisher, x11 = deVect, x21 = totalDE-deVect,
x12 = ndeVect, x22 = totalGenes-totalDE-ndeVect)
    orderp <- order(correctedRanking)
    # orderedTitles <- path.titles[orderp]

glists <- sapply(colnames(emmatrixDEMod), function(x)
rownames(emmatrixDEMod)[emmatrixDEMod[,x]==1])

respwresized <- data.frame("ID"=names(deVect)[orderp], pvalues =
correctedRanking[orderp], "p.adj(fdr)" = p.adjust(correctedRanking[orderp], 'fdr'),
"de"=deVect[orderp], "size"=deVect[orderp]+ndeVect[orderp],
"genes"=sapply(glists, paste, collapse=";")[orderp])

save(respwresized, file='pwresizedd7d0_V3_SPIA180.RData')
    write.table(respwresized, file="pwresized_d7d0_xtresh10p_spia180.RData")

=============== pinters <- function(data, i, j){
    inters <- data[(data[,i]==1) & (data[,j]==1),c(1,i,j)]
    dimInters <- dim(inters)[1]
    deinters <- length(inters[inters$DE ==1,'DE'])
```

```
    ndeinters <- length(inters[inters$DE == 0,'DE'])
    deGenes <- sum(data$DE)
    totGenes <- dim(data)[1]
    pinters <- doFisher(deinters, deGenes-deinters, ndeinters, totGenes-deGenes-dimInters+deinters)
    pinters
} pvalcm <- function(data,i,j){
    cm <- data[data[,i]==1 & data[,j]==0,c(1,i)]
    dimcm <- dim(cm)[1]
    decm <- sum(cm[,"DE"])
    ndecm <- dimcm-decm
    deGenes <- sum(data$DE)
    totGenes <- dim(data)[1]
    pcm <- doFisher(decm,deGenes - decm, ndecm, totGenes - decm - ndecm)
    pcm
} doFisher <- function(x11,x21,x12,x22){
    mat <- matrix(c(x11,x21,x12,x22),2)
    tfres <- fisher.test(mat, alternative="greater")
    doFisher <- tfres$p.value
    doFisher
} doChi <- function(x11,x21,x12,x22){
  mat <- matrix(c(x11,x21,x12,x22),2)
  tcres <- chisq.test(mat)
  doChi <- tcres$p.value
  doChi
} zeroRow <- function(x){
    if(sum(x) != 0){
        for(i in 1:length(x)){
            if(x[i] < max(x))
```

```
                x[i]=0
            if(x[i] == max(x))
                x[i]=1
        }
    }
    x
} compPi <- function(row, pi){
    if(sum(row) != 0){
        row * pi/ sum(row*pi)
    }else{
        row
    }
}

===============

# ----- Define a function for plotting a matrix ----- #
myImagePlot <- function(x, threshold1p=NULL, threshold5p=NULL, cex.axis.matrix=0.5, ...){
    min <- min(x)
    max <- max(x)
    yLabels <- rownames(x)
    xLabels <- colnames(x)
    title <-c()
    ## check for additional function arguments
    if( length(list(...)) ){
      Lst <- list(...)
      if( !is.null(Lst$zlim) ){
        min <- Lst$zlim[1]
        max <- Lst$zlim[2]
      }
      if( !is.null(Lst$yLabels) ){
        yLabels <- c(Lst$yLabels)
      }
      if( !is.null(Lst$xLabels) ){
        xLabels <- c(Lst$xLabels)
      }
```

```
    if( !is.null(Lst$title) ){
      title <- Lst$title
    }
  }
}
check for null values
if( is.null(xLabels) ){
  xLabels <- c(1:ncol(x))
}
if( is.null(yLabels) ){
  yLabels <- c(1:nrow(x))
}
Original layout
layout(matrix(data=c(1,2),  nrow=1,  ncol=2),  widths=c(4,1),
heights=c(1,1))
  layout(matrix(data=c(1,2), nrow=1, ncol=2), widths=c(15,1), heights=c(1,1))

from green to red
ColorRamp <- rgb( seq(0,1,length=256), # Red
          seq(1,0,length=256), # Green
          seq(0,0,length=256))
              # Blue
ColorRamp <- c( rgb(seq(1,.5,length=26), # Red
seq(1,1,length=26), # Green
seq(1,.5,length=26)),
rgb(seq(.5,0,length=6), # Red
seq(1,1,length=6), # Green
seq(.5,0,length=6)),
rgb(seq(0,.5,length=20), # Red
seq(1,.5,length=20), # Green
seq(0,0,length=20)),
rgb(seq(.5,1,length=204), # Red
seq(.5,0,length=204), # Green
seq(0,0,length=204)))
from green to white to red
ColorRamp <- c( rgb(seq(0,.5,length=30), # Red
seq(1,1,length=30), # Green
seq(0,.5,length=30)),
rgb(seq(.5,1,length=6), # Red
seq(1,1,length=6), # Green
```

```
seq(.5,1,length=6)),
rgb(seq(1,.5,length=17),   # Red
seq(1,0,length=17),    # Green
seq(1,0,length=17)),
rgb(seq(.5,1,length=203),  # Red
seq(0,0,length=203),   # Green
seq(0,0,length=203)))

cut <- 120
ColorRamp <- c( rgb(seq(1,0.8,length=cut),   # Red
seq(1,.5,length=cut),   # Green
seq(1,.5,length=cut)),
rgb(seq(0.8,1,length=256-cut),  # Red
seq(.5,0,length=256-cut),   # Green
seq(.5,0,length=256-cut)))

ColorLevels <- seq(min, max, length=length(ColorRamp))

Reverse Y axis
reverse <- nrow(x) : 1
yLabels <- yLabels[reverse]
x <- x[reverse,]

Data Map
topm <- 8.5
botm <- 1
par(mar = c(botm,6,topm,1))
image(1:length(xLabels), 1:length(yLabels), t(x), col=ColorRamp, xlab="",
    ylab="", axes=FALSE, zlim=c(min,max))

if(!is.null(threshold1p)){
  abline(v=threshold1p[1], col='blue')
  abline(h=threshold1p[2], col='blue')
}
if(!is.null(threshold5p)){
  abline(v=threshold5p[1])
  abline(h=threshold5p[2])
}
```

```
if( !is.null(title) ){
  title(main=title)
} axis(TOP<-3,      at=1:length(xLabels),      labels=xLabels,
cex.axis=cex.axis.matrix, cex=cex.axis.matrix, las=VERTICAL <- 2)
     axis(LEFT      <-2,      at=1:length(yLabels),      labels=yLabels,
cex.axis=cex.axis.matrix, cex=cex.axis.matrix, las=HORIZONTAL<-1)

Color Scale
par(mar = c(botm,.8,topm,1))
image(1, ColorLevels,
     matrix(data=ColorLevels, ncol=length(ColorLevels),nrow=1),
     col=ColorRamp,
     xlab="",ylab="",
     xaxt="n", cex.axis=0.8)

layout(1)
}
----- END plot function ----- #

=============== kegglink <- function(pwt1, pwt2, organism, overlapMatrix, pathwayData, geneSel){
    organismString = paste(organism,":",sep="")
   pathway.names <- rownames(overlapMatrix$overlap)
   ovMatrix <- overlapMatrix$overlap
   deMatrix <- overlapMatrix$degenes
   if(is.character(pwt1)){
     pw1 <- which(pathway.names == pwt1)
   }else{
     pw1 <- pwt1
   }
   if(is.character(pwt2)){
     pw2 <- which(pathway.names == pwt2)
   }else{
     pw2 <- pwt2
```

```
}
pw1.genes <- pathwayData[[pw1]]
pw2.genes <- pathwayData[[pw2]]
pw1.de <- geneSel[geneSel %in% pw1.genes]
pw1.de <- pw1.de[!pw1.de %in% pw2.genes]
pathway <- pathway.names[pw1]
ovgenes <- ovMatrix[pw1, pw2]
ovgenes <- ovgenes[[1]]
degenes <- deMatrix[pw1, pw2]
degenes <- degenes[[1]]
ovgenes <- ovgenes[!(ovgenes %in% degenes)]
pwGenes <- paste(organismString,pw1.de, sep='')
pwGenes <- paste(pwGenes,"%09default,red/", sep='')
pwGenes <- paste(pwGenes, collapse='')
overlapGenes <- paste(organismString,ovgenes, sep='')
overlapGenes <- paste(overlapGenes, "%09yellow,black/", sep='')
overlapGenes <- paste(overlapGenes,collapse="")
overlapDeGenes <- paste(organismString,degenes, sep='')
overlapDeGenes <- paste(overlapDeGenes,"%09yellow,red/", sep='')
overlapDeGenes <- paste(overlapDeGenes,collapse="")
genes <- paste(pwGenes,overlapGenes,overlapDeGenes, sep='')
link       <-       paste(c("http://www.genome.jp/kegg-bin/mark_pathway_www?@",organism,pathway,"/default%3dyellow/"), collapse="")
link <- paste(link,genes, sep='')
#browseURL(link)
kegglink <- link
kegglink
} keggLinkModule <- function(de, nde, pathwayID, organism){
  organismString <- paste(organism,":",sep="")
  ndeString <- paste(organismString,nde, sep="")
  ndeString <- paste(ndeString, "%09yellow,black/", sep='')
  ndeString <- paste(ndeString, collapse="")
  deString <- paste(organismString, de, sep="")
  deString <- paste(deString, "%09yellow,red/", sep='')
  deString <- paste(deString, collapse='')
  genes <- paste(deString, ndeString, collapse="")
```

```
    link          <-          paste(c("http://www.genome.jp/kegg-
bin/mark_pathway_www?@",organism,pathwayID,"/default%3dyellow/"),
collapse="")
    link <- paste(link,genes, sep=")
    keggLinkModule <- link
    keggLinkModule
  }

============== linksMatrix <- function(objectCrossTalk, organism=NULL, toHtml=TRUE,
htmlTableName=NULL){ if(toHtml & is.null(htmlTableName))
      stop("when toHtml==TRUE htmlTableName must be true")
    noPathways <- dim(objectCrossTalk$heatmap$map)[1]
    source("~/Workspaces/xtalk/r_utils/kegglink.R")
    linksMatrix <- matrix("", noPathways, noPathways)
    pathway.data <- NULL
    if(is.null(organism))
      organism <- "hsa"
    for(i in 1:noPathways){
      for(j in 1:noPathways){
        linksMatrix[i,j] <- kegglink(i,j,organism, objectCrossTalk$overlapData,
objectCrossTalk$pathwaysInfo[[1]], sel)
      }
    } paste1 <- matrix(paste("<a href='", linksMatrix, sep=""), noPathways,
noPathways)
    paste2 <- matrix(paste(paste1, "'>k</a>", sep=""), noPathways,
noPathways)

colnames(paste2) <- colnames(objectCrossTalk$heatmap$map)
    rownames(paste2) <- rownames(objectCrossTalk$heatmap$map)

if(toHtml){
      library(R2HTML)
      header <- readLines("~/Workspaces/xtalk/r_utils/linksMatrix_head.html")
```

```
    writeLines(header, con=htmlTableName)
    HTML(data.frame(paste2),           file=htmlTableName,        classfirstline=
'verticalText', classfirstcolumn='horizontalLabel', append=TRUE)
    cat(c("</body>", '\n', "</html>"), file=htmlTableName, append=TRUE)
  }
  linksMatrix <- paste2
  linksMatrix
}

=============== logL <- function(emmat, prob){
    ## this is the logLikelyhood value, and it can be used as a stop criteria
    sumi <- apply(emmat,2,sum)
    sumi <- prob * sumi
    logL = sum(sumi)
} mieMatrices   <-   function(deData,   pathwayData,   stopThreshold=1e-5,
xThreshold=0.1, verbose=F, correctDESize=F, correctNDESize=F){ sel <- names(deData)[deData]
   ref <- names(deData)

pSize <- unlist(lapply(pathwayData,function(x){sum(ref %in% x)}))
   pDE <- unlist(lapply(pathwayData,function(x){sum(sel %in% x)}))
   pNDE <- pSize-pDE phyp <- mapply(doFisher, x11 = pDE, x21 = sum(deData)-pDE, x12 = pSize
- pDE, x22 = length(deData)-pSize-length(   sel)+pDE)

how.many.pws <- length(pathwayData)
      emmatrix <- matrix(0,nrow=length(deData), ncol=how.many.pws+1)
      rownames(emmatrix) <- names(deData)
      colnames(emmatrix) <- c("DE", names(pathwayData))
      emmatrix <- as.data.frame(emmatrix)
      emmatrix[,1] = as.numeric(deData)
    ## CHECK THIS BECAUSE IT IS THE SLOWEST PART
      for(i in 2:(how.many.pws+1)){
```

```
            emmatrix[,i] <- as.numeric(names(deData) %in% pathwayData[[i-
1]])
        } originalEMMatrixDE <- emmatrix[emmatrix$DE == 1, 2:dim(emmatrix)[2]]
    originalEMMatrixNDE <- emmatrix[emmatrix$DE == 0, 2:dim(emmatrix)[2]]

cat(c("\n pathways under xT: ", sum(phyp<xThreshold), '\n'))

emmatrix <- emmatrix[,c(1,which(phyp<xThreshold)+1)]
pSizes <- apply(emmatrix[,2:dim(emmatrix)[2]], 2, sum)
    if(!is.null(dim(emmatrix))){
        emmatrixDE <- emmatrix[emmatrix$DE == 1, 2:dim(emmatrix)[2]]
        emmatrixNDE <- emmatrix[emmatrix$DE == 0, 2:dim(emmatrix)[2]]
    }else{
      emmatrixDE <- NULL
      emmatrixNDE <- NULL
    } if(!is.null(dim(emmatrixDE))){
      pSizes <- apply(emmatrix[,2:dim(emmatrix)[2]], 2, sum)

rnamesde <- rownames(emmatrixDE)
      rnamesnde <- rownames(emmatrixNDE)

DE matrix
        ### initial vector of pi
    pi0 <- apply(emmatrixDE, 2, sum) / sum(emmatrixDE)
    piPrev <- pi0
    piNext <- rep(0,length(pi0))
    count <- 1 while(sqrt(sum((piPrev-piNext)^2)) > stopThreshold){
        if(verbose) cat(count, sqrt(sum((piPrev-piNext)^2)), '\n')
        ## the following line can be used in multicore environments; it doesn't
improve the performance though; needs the package multicore loaded
        # emmatrixDE <- t(sapply(mclapply(data.frame(t(emmatrixDE)),compPi,
pi=piPrev, mc.cores=2), function(x) x))
```

```
        emmatrixDE    <-    t(sapply(lapply(data.frame(t(emmatrixDE)),compPi,
pi=piPrev), function(x) x))
        piNext <- piPrev
        ## if I need to normalize by the size of the pathway I should do it here, no?
        piPrev <- apply(emmatrixDE, 2, sum) / sum(emmatrixDE)
        if(correctDESize){
          piPrev <- piPrev/pSizes
        }
        count <- count + 1
        if(verbose) print(count)
      }

NDE matrix
      ### initial vector of pi
      pi0 <- apply(emmatrixNDE, 2, sum) / sum(emmatrixNDE)
      piPrev <- pi0
      piNext <- rep(0,length(pi0))
      count <- 1 while(sqrt(sum((piPrev-piNext)^2)) > stopThreshold){
        if(verbose) cat(count, sqrt(sum((piPrev-piNext)^2)), '\n')
        ## the following line can be used in multicore environments; it doesn't improve the performance though; needs the package multicore loaded emmatrixNDE    <-
t(sapply(mclapply(data.frame(t(emmatrixNDE)),compPi, pi=piPrev, mc.cores=2), function(x) x))
        emmatrixNDE    <-    t(sapply(lapply(data.frame(t(emmatrixNDE)),compPi,
pi=piPrev), function(x) x))
        piNext <- piPrev
        piPrev <- apply(emmatrixNDE, 2, sum) / sum(emmatrixNDE)
        if(correctNDESize){
          piPrev <- piPrev/pSizes
        }
        count <- count + 1
      } rownames(emmatrixDE) <- rnamesde
```

```
    rownames(emmatrixNDE) <- rnamesnde
    colnames(emmatrixDE)       <-      colnames(emmatrixNDE)       <-
colnames(emmatrix)[2:(dim(emmatrix)[2])]

} originalEMMatrixDE[,colnames(emmatrixDE)] <- emmatrixDE
    originalEMMatrixNDE[,colnames(emmatrixNDE)] <- emmatrixNDE mie   <-   list(EMMatrixDE = originalEMMatrixDE, EMMatrixNDE =
originalEMMatrixNDE, phyper=phyp)

return(mie)

}

=============== inRef <- function(x,reference){
    inRef <- sum(x %in% reference)
    inRef
} fisherset <- function(set,ref,sel){
    path <- set[set %in% ref]
    cmvect <- c(
            sum(path %in% sel),
            sum(!path %in% sel),
            length(sel)-sum(path %in% sel) ,
            length(ref[!(ref %in% path) & !(ref %in% sel)])
            )
    cmatrix <- matrix(cmvect,nrow=2)
    fres <- fisher.test(cmatrix, alternative='g')
    fisherset <- fres$p.value
    fisherset
} jaccardd <- function(x,y){
```

```
    jaccardd <- 1 - length(intersect(x,y))/min(length(x),length(y))
    jaccardd
} collapseNames <- function(modName, pNamesIds){
    pnames <- pNamesIds[unlist(strsplit(modName," "))]
    pnames <- gsub(" ","",pnames)
    pnames <- substr(pnames,1,8)
    pnames <- paste(pnames,collapse="+")
} addModules <- function(pathwayData, ref, sel, pathwayTitles, thresholds, distanceThreshold, verbose=TRUE){
    # thresholds are the thresholds we want to test in the form of a vector with the numeric thresholds.
    ## e.g.: c(0.01, 0.05)
    # distanceThreshold is the threshold under which modules are merged
    pvals <- sapply(pathwayData, fisherset, ref=ref, sel=sel)
    orderp <- order(pvals)
    pvals <- pvals[orderp]
    pvals <- p.adjust(pvals,'fdr')

#thrs <- c(max(which(pvals< 0.01)), max(which(pvals< 0.05)))
    thrs <- NULL for(i in 1:length(thresholds)){
        thrs <- c(thrs, max(which(pvals < thresholds[i])))
    }
    names(thrs) <- thresholds
    thrs <- thrs[!duplicated(thrs)]
    thrs <- thrs[!is.infinite(thrs)]
    if(length(thrs)==0){
        moduleList = NULL
        cat("There is no significant pathway for any of the specified thresholds. No modules will be found at this stage.")
        return(list(pathways=pathwayData, titles=c(pathwayTitles)))
    }
    pNamesIds <- pathwayTitles[orderp]
```

```
pathwayDataOrdered <- pathwayData[orderp]
names(pNamesIds) <- names(pathwayDataOrdered)
if(verbose) cat("pNameIds generated, searching for modules\n")
moduleList <- list()

for(t in 1:length(thrs)){
        threshold <- as.numeric(names(thrs)[t])
        if(verbose) cat("searching threshold", t, ":", names(thrs)[t], '\n')
        if(t == 1){
                start = 1
                }else{
                        start <- thrs[t-1]
                }
        for(i in start:thrs[t]){
                for(j in start:thrs[t]){
                        if(i < j){ creation of the three pathways
                                bait <- pathwayDataOrdered[[i]]
                                prey <- pathwayDataOrdered[[j]]
                                #those are the new pathways to be created
                                baitcm <- bait[!bait %in% prey]
                                preycm <- prey[!prey %in% bait]
                                overlap <- bait[bait %in% prey]

pDataTemp <- pathwayDataOrdered
                                pDataTemp[[i]] <- baitcm
                                namei   <-   paste(names(pDataTemp)[i],   'minus', names(pDataTemp)[j])
                                namej   <-   paste(names(pDataTemp)[j],   'minus', names(pDataTemp)[i])
                                nameo   <-   paste(names(pDataTemp)[i],   'overlap', names(pDataTemp)[j])
                                names(pDataTemp)[i] <- namei
                                pDataTemp[[j]] <- preycm
                                names(pDataTemp)[j] <- namej
                                pDataTemp[[length(pDataTemp)+1]] <- overlap
                                names(pDataTemp)[length(pDataTemp)] <- nameo
                                # now the list is modified, I compute the pvalues
```

```
                    pvalues    <-    sapply(pDataTemp,fisherset,ref=ref, sel=sel)
                    # correct pathways and determine if i is not significant anymore, j is not significant anymore, and overlap is significant (I will use threshold 1 now, but I can use both)
                    padj <- p.adjust(pvalues, 'fdr')

if( (padj[length(padj)] <= threshold) & (padj[i] > threshold) & (padj[j] > threshold) ){
                        ## the overlap is significant, the crescent moons are not
                        ## now I need to check if there is another pathway other than i and j in which the overlap is moduleList[[length(moduleList)+1]] <- overlap
                        names(moduleList)[length(moduleList)] <- nameo

}

}
                ## if(verbose) cat(i,j,'\n')
                if(verbose) cat('*')
            }
        }
        if(verbose) cat('\n')
    }
    if(length(moduleList)==0){
        moduleList <- NULL
        cat("No modules found!")
        return(list(pathways=pathwayData, titles=pathwayTitles))
    }
    if(verbose) cat("computing jaccard matrix\n")
    jaccardMatrix    <-    matrix(1,nrow=length(moduleList), ncol=length(moduleList))
    for(i in 1:length(moduleList)){
        for(j in 1:length(moduleList)){
            jaccardMatrix[i,j] <- jaccardd(moduleList[[i]], moduleList[[j]])
        }
```

```
}
if(verbose) cat("merging modules\n")
jaccardMatrixTmp <- jaccardMatrix
moduleListTmp <- moduleList
endIt <- FALSE
count <- 1
while(!endIt){
skip=FALSE
        ## if(verbose) cat(count,'\n')
        endIt <- TRUE
        for(i in 1:length(moduleListTmp)){
                for(j in 1:length(moduleListTmp)){
                        if(verbose) cat('*')
                        if(j > i){
                                if( (jaccardMatrixTmp[i,j] < distanceThreshold)
& ( jaccardMatrixTmp[i,j] == min(jaccardMatrixTmp[upper.tri(jaccardMatrixTmp)])
) ){
                                        # this means that there is a change in the matrix: two modules will merge
                                        moduleName <- paste(names(moduleListTmp)[i], names(moduleListTmp)[j])
                                        newModule <- union(unlist(moduleListTmp[[i]]), unlist(moduleListTmp[[j]]))
                                        moduleListTmp <- moduleListTmp[-c(i,j)]

moduleListTmp[[length(moduleListTmp)+1]] <- newModule names(moduleListTmp)[length(moduleListTmp)] <- moduleName
                                        # we will skip the remaining modules, we will see in the next
                                        skip <- TRUE
                                        endIt <- FALSE
                                        break
                                }
                        }
                }
        }
        if(skip){
                jaccardMatrixTmp <- matrix(1,nrow=length(moduleListTmp), ncol=length(moduleListTmp))
```

```
            for(i in 1:length(moduleListTmp)){
                for(j in 1:length(moduleListTmp)){
                    jaccardMatrixTmp[i,j]                    <-
jaccardd(moduleListTmp[[i]], moduleListTmp[[j]])
                }
            }
            skip = FALSE
            break
            }
        }
        cat(count,'\n')
        count <- count+1
    }
    if(verbose) cat ('\n')
    if(verbose) cat("cleaning names\n")
    namesList   <-   lapply(names(moduleListTmp),function(x)   strsplit(gsub("
overlap "," ",x)," "))
    removals <- lapply(namesList, function(x) sort(unique(unlist(x))))
    namesList   <-   sapply(namesList,function(x)   paste(sort(unique(unlist(x))),
collapse=' '))
    names(moduleListTmp) <- namesList

#Remove module i from pathways with ID in removals[i]
    modulesTitles   <-   unlist(lapply(names(moduleListTmp),   collapseNames,
pNamesIds=pNamesIds))
    if(verbose) cat("removing modules from parent pathways\n")
    pathwayDataMod <- pathwayDataOrdered
    for(i in 1:length(pathwayDataMod)){
        for(j in 1:length(moduleListTmp)){
            if(names(pathwayDataMod)[i] %in% removals[[j]]){
                pathwayDataMod[[i]]                          <-
setdiff(pathwayDataMod[[i]],moduleListTmp[[j]])
                pNamesIds[names(pathwayDataMod)[i]] <- paste("*",
pNamesIds[names(pathwayDataMod)[i]])
            }
        }
    }
    pathwayDataMod <- c(pathwayDataMod, moduleListTmp)
```

```
names(pathwayDataMod) <- c(pNamesIds, modulesTitles)
   names(modulesTitles) <- names(moduleListTmp)
   addModules <- list(pathways=pathwayDataMod, titles=c(pNamesIds, modulesTitles))
}
```

================

```
overlaps <- function(pathway.list, geneSel){
  n.pathways <- length(pathway.list)
  pathway.names <- names(pathway.list)
  res.list <- list()
  overlap <- list()
  deoverl <- list()
  for(i in 1:n.pathways){
    bait.genes <- pathway.list[[i]]
    nde.bait <- sum(bait.genes %in% geneSel)
    for(j in 1:n.pathways){
      prey.genes <- pathway.list[[j]]
      nde.prey <- sum(prey.genes %in% geneSel)
      overlap.genes <- bait.genes[bait.genes %in% prey.genes]
      nde.overlap <- sum(overlap.genes %in% geneSel)
      overlap[[(j-1)*n.pathways+i]] <- overlap.genes
      deoverl[[(j-1)*n.pathways+i]] <- overlap.genes[overlap.genes %in% geneSel]
    }
  }
  overlap.genes <- matrix(overlap, nrow=n.pathways, byrow=TRUE)
  overlap.deg <- matrix(deoverl, nrow=n.pathways, byrow=TRUE)
  rownames(overlap.genes) <- rownames(overlap.deg) <- colnames(overlap.genes) <- colnames(overlap.deg) <- pathway.names
  res.list$overlap <- overlap.genes
  res.list$degenes <- overlap.deg
  res.list
}
```

What is claimed is:

1. A system comprising:
at least one processor and
a memory coupled to the at least one processor,
wherein the memory stores:
a node data structure including a plurality of nodes, wherein each node of the plurality of nodes has a corresponding measured difference;
a pathway data structure including a plurality of pathways, wherein each pathway of the plurality of pathways includes a set of nodes, and wherein the set of nodes for each pathway is linked to other nodes based on known interactions between the nodes;
a data structure including, for each pathway of the plurality of pathways, a P-value indicating the probability of observing measured differences on that pathway;
instructions for execution by the at least one processor, and
wherein the instructions include:
for a first pathway and a second pathway, computing, for each pathway, a first P-value indicating a probability of observing measured differences on that pathway;
identifying a set of intersecting nodes, wherein the set of intersecting nodes are included in a first set of nodes corresponding to the first pathway and a second set of nodes corresponding to the second pathway;
for the first pathway and the second pathway, computing a second P-value indicating a probability of observing the measured differences on that pathway when the set of intersecting nodes is removed;
in response to the first P-value of the first pathway being lower than the second P-value of the first pathway and the first P-value of the second pathway being lower than the second P-value of the second pathway, generating and displaying an indication that an independent functional module is present between the first pathway and the second pathway, wherein the independent functional module includes many or all of the common nodes between the two pathways, and wherein a treatment for a physical condition associated with at least one of the first pathway and the second pathway is identified based on the independent functional module;
determining a crosstalk based on a comparison of the second P-value of the second pathway and the first P-value of the second pathway when a result of comparison of the second P-value of the first pathway and the first P-value of the first pathway is unchanged; and
facilitating treatment of a patient for the physical condition associated with the at least one of the first pathway and the second pathway, in response to computing the independent functional module.

2. The system of claim 1 wherein the instructions include:
in response to the second P-value of the first pathway being unchanged compared to the first P-value of the first pathway and the second P-value of the second pathway being unchanged compared to the first P-value of the second pathway, generating and displaying an indication that crosstalk is not present.

3. The system of claim 1 wherein the instructions include:
in response to the second P-value of the first pathway being unchanged compared to the first P-value of the first pathway and the second P-value of the second pathway decreasing compared to the first P-value of the second pathway, generating and displaying an indication that crosstalk is present.

4. The system of claim 1 wherein the instructions include:
in response to the second P-value of the first pathway being unchanged compared to the first P-value of the first pathway and the second P-value of the second pathway increasing compared to the first P-value of the second pathway, generating and displaying an indication that crosstalk is present.

5. The system of claim 1 wherein the instructions include:
generating and displaying a heat map illustrating the P-value changes when common genes are eliminated between pairs of pathways.

6. The system of claim 5 wherein:
the heat map indicates a rank of pathways based on their probabilities of being impacted by a corresponding phenotype.

7. The system of claim 1 wherein the instructions include:
computing the first P-values for each pathway based on measured differences of their nodes, using a pathway analysis algorithm including at least one of: an over-representation approach (ORA), a gene set enrichment analysis (GSEA), gene set analysis (GSA), and PADOG.

8. The system of claim 1 wherein the instructions include:
computing the P-values using a pathway analysis statistical modeling algorithm that calculates a probability of the number and/or distribution of observed measurements in a pathway by comparing the observed measurements with the number and/or distribution of the measurements expected by chance.

9. The system of claim 1 wherein the instructions include:
computing the P-values using a functional scoring algorithm that calculates a score reflecting a degree to which a given pathway correlates to a given phenotype.

10. The system of claim 1 wherein the instructions include:
computing the P-values using an impact analysis algorithm that calculates a P-value that includes information on a position of a node within a particular pathway, all its interactions with other nodes, and the measured difference of all nodes on the given pathway.

11. The system of claim 1 wherein the node data structure includes data corresponding to genes and the measured difference is data reflecting an expression state of an associated gene, as measured by methylation state, mRNA levels, and protein abundance.

12. The system of claim 1 wherein the node data structure includes data selected from a group consisting of one or more of: genes, methylation values, transcripts, gene products, RNA, and proteins.

13. A method comprising:
for a first pathway and a second pathway, computing, for each pathway, a first P-value indicating a probability of observing measured differences on that pathway just by chance, wherein:
a node data structure includes a plurality of nodes,
each node of the plurality of nodes has a corresponding measured difference,
a pathway data structure includes a plurality of pathways,
each pathway of the plurality of pathways includes a set of nodes,
the set of nodes for each pathway is linked to other nodes based on known interactions between the nodes, and
a data structure includes, for each pathway of the plurality of pathways, a P-value indicating the probability of observing measured differences on that pathway just by chance;

identifying a set of intersecting nodes, wherein the set of intersecting nodes are included in a first set of nodes corresponding to the first pathway and a second set of nodes corresponding to the second pathway;

for the first pathway and the second pathway, computing a second P-value indicating a probability of observing the measured differences on that pathway just by chance when the set of intersecting nodes is removed; and in response to the first P-value of the first pathway being lower than the second P-value of the first pathway and the first P-value of the second pathway being lower than the second P-value of the second pathway, generating and displaying an indication that an independent functional module is present between the first pathway and the second pathway, wherein the independent functional module that includes many or all of the common nodes between the two pathways, and wherein a treatment for a physical condition associated with at least one of the first pathway and the second pathway is identified based on the independent functional module;

determining a crosstalk based on a comparison of the second P-value of the second pathway and the first P-value of the second pathway when a result of comparison of the second P-value of the first pathway and the first P-value of the first pathway is unchanged; and facilitating treatment of a patient for the physical condition associated with the at least one of the first pathway and the second pathway, in response to computing the independent functional module.

14. The method of claim 13 further comprising:
in response to the second P-value of the first pathway being unchanged compared to the first P-value of the first pathway and the second P-value of the second pathway being unchanged compared to the first P-value of the second pathway, generating and displaying an indication that crosstalk is not present.

15. The method of claim 13 further comprising:
in response to the second P-value of the first pathway being unchanged compared to the first P-value of the first pathway and the second P-value of the second pathway decreasing compared to the first P-value of the second pathway, generating and displaying an indication that crosstalk is present.

16. The method of claim 13 further comprising:
in response to the second P-value of the first pathway being unchanged compared to the first P-value of the first pathway and the second P-value of the second pathway increasing compared to the first P-value of the second pathway, generating and displaying an indication that crosstalk is present.

17. The method of claim 13 further comprising:
in response to the second P-value of the first pathway being unchanged compared to the first P-value of the first pathway and the second P-value of the second pathway increasing compared to the first P-value of the second pathway, generate and display an indication that crosstalk is present.

18. The method of claim 13 further comprising:
in response to the second P-value of the first pathway being unchanged compared to the first P-value of the first pathway and the second P-value of the second pathway decreasing compared to the first P-value of the second pathway, generating and displaying an indication that crosstalk is present.

* * * * *